US011806380B2

(12) United States Patent
Tuan et al.

(10) Patent No.: US 11,806,380 B2
(45) Date of Patent: Nov. 7, 2023

(54) METHOD AND COMPOSITION FOR PREVENTING AND TREATING COVID-19 AND LONG COVID

(71) Applicant: GLOBAL PREVENTIVE MEDICINE BIOTECH COMPANY LIMITED, New Taipei (TW)

(72) Inventors: Mei-Nan Tuan, Taipei (TW); Hien Ly Doan, Taipei (TW); Zi-Yi Huang, Kaohsiung (TW); Chia-Yin Lee, Douliu (TW); Thuc Anh Nguyen, Taipei (TW)

(73) Assignee: GLOBAL PREVENTIVE MEDICINE BIOTECH COMPANY LIMITED, New Taipei (TW)

( * ) Notice: Subject to any disclaimer, the term of this patent is extended or adjusted under 35 U.S.C. 154(b) by 0 days.

(21) Appl. No.: 17/834,215

(22) Filed: Jun. 7, 2022

(65) Prior Publication Data

US 2022/0387541 A1 Dec. 8, 2022

Related U.S. Application Data

(60) Provisional application No. 63/277,774, filed on Nov. 10, 2021, provisional application No. 63/197,701, filed on Jun. 7, 2021.

(51) Int. Cl.

| | |
|---|---|
| ***A61K 36/82*** | (2006.01) |
| ***A61K 36/87*** | (2006.01) |
| ***A61K 36/185*** | (2006.01) |
| ***A61K 36/63*** | (2006.01) |
| ***A61K 36/28*** | (2006.01) |
| ***A61P 31/14*** | (2006.01) |
| ***A61K 36/48*** | (2006.01) |
| ***A61K 31/353*** | (2006.01) |
| ***A61K 31/7048*** | (2006.01) |
| ***A61K 31/352*** | (2006.01) |
| ***A61K 31/05*** | (2006.01) |
| ***A61K 31/716*** | (2006.01) |

(52) U.S. Cl.

CPC .............. *A61K 36/82* (2013.01); *A61K 31/05* (2013.01); *A61K 31/352* (2013.01); *A61K 31/353* (2013.01); *A61K 31/7048* (2013.01); *A61K 31/716* (2013.01); *A61K 36/185* (2013.01); *A61K 36/28* (2013.01); *A61K 36/48* (2013.01); *A61K 36/63* (2013.01); *A61K 36/87* (2013.01); *A61P 31/14* (2018.01)

(58) Field of Classification Search

None

See application file for complete search history.

(56) References Cited

FOREIGN PATENT DOCUMENTS

WO WO 2011003045 A1 * 1/2011

* cited by examiner

*Primary Examiner* — Michael V Meller

(74) *Attorney, Agent, or Firm* — Birch, Stewart, Kolasch & Birch, LLP

(57) ABSTRACT

Coronavirus Disease 2019 (COVID-19) remains a threat with the emergence of new variants, especially Delta and Omicron, without specific effective therapeutic drugs. The present invention provides a method and a composition for preventing and treating COVID-19 (SARS-CoV-2) coronavirus infection which includes administering to a subject in need thereof one or more therapeutically effective doses of Virofree which comprises a pharmaceutically acceptable combination of grape seed extract, acerola cherry extract, olive leaf extract, marigold extract, green tea extract, pomegranate extract, yeast beta-glucan and soya bean extract for a treatment period.

4 Claims, 20 Drawing Sheets

METHOD AND COMPOSITION FOR PREVENTING AND TREATING COVID-19 AND LONG COVID

CROSS REFERENCE

This non-provisional application claims the priority under 35 U.S.C. § 119(a) on U.S. Patent Provisional Application Nos. 63/197,701 filed on Jun. 7, 2021, and 63/277,774 filed on Nov. 10, 2021, the entire contents of which are hereby incorporated by reference.

FIELD OF THE INVENTION

The present invention is pertaining to a method and a composition for preventing and treating an antiviral infection in mammals, particularly COVID-19 (an SARS-CoV-2 Infection) and Long COVID.

BACKGROUND OF THE INVENTION

Since a novel coronavirus, known as SARS-CoV-2, broke out in late 2019, it has rapidly become a pandemic that the World Health Organization has declared an emergency issue. Clinical features revealed that patients presented short-term pneumonia [1] and then progressed to multi-organ failure [2] in severe patients, coronaviruses induce inflammatory responses and associated lymphopenia [3]. The attachment of SARS-CoV-2 spike protein to the ACE2 receptor promotes the viral entry, replication, new virion formation then release the new viral particles which initiate dysregulation of inflammation and cytokine storm [4]. Severe COVID-19 patients suffer from cytokine storms, leading to the fatal ARDS with an incidence rate of 41.8%, or irreversible pulmonary fibrosis [5]. Such uncontrolled systemic hyper-inflammation can be regulated by two primary mediators: ferritin and miRNA. Previous publications have shown that increasing ferritin levels in severe patients [6] and their miRNAs' profiles deeply involved the high expression of cytokines [7, 8]. Although COVID-19 progression and the underlying mechanisms were identified, only 11 emergency treatments and merely 2 approved drugs are used [9]. All of these current drugs are designed for a single target or a mechanism of action, for example, Remdesivir is an anti-virus replication drug while Baricitinib and Tocilizumab are immunomodulators. However, SARS-CoV-2 induced the intricate signaling that blocking a single function caused poor therapeutic efficiency. The emergence of new mutant strains including Alpha (α), Beta (β), Gamma (γ), Delta (δ), and Omicron (o), which have a 50% higher rate of transmission and infection than the wild Wuhan SARS-CoV-2 has raised concerns about the efficacy of vaccines [10]. Therefore, discovering multifunction drugs is highly concerned.

It is desirable to develop an effective therapy or a therapeutic agent for treating and/or preventing Covid-19 and/Long Covid.

SUMMARY OF THE INVENTION

The present invention relates to a method and a composition for preventing and treating Covid-19, i.e., an infection of SARS-CoV-2, and Long Covid.

In one aspect, the invention provides a method for treating or preventing Covid-19 and long Covid in a subject, which comprises administering to said subject a therapeutically effective amount of a herbal composition comprising a mixture of grape seed extract, acerola cherry extract, olive leaf extract, marigold extract, green tea extract, pomegranate extract, yeast beta-glucan and soya bean extract.

In another aspect, the invention provides a composition for treating or preventing Covid-19 and/or long Covid, comprising a mixture of grape seed extract, acerola cherry extract, olive leaf extract, marigold extract, green tea extract, pomegranate extract, yeast beta-glucan and soya bean extract.

According to the invention, the herabal composition of the invention comprises the active ingredients isolated from the herbal composition, including quercetin, hesperidin, genistein, daidzein, and resveratrol.

In one example of the invention, the composition of the present invention (called as "the herbal composition" hereinafter) comprises 10 wt %-50 wt % of grape seed extract, 5 wt %-30 wt % of acerola cherry extract, 5 wt %-30 wt % of olive leaf extract, 1 wt %-20 wt % of marigold extract, 1 wt %-20 wt % of green tea extract; 1 wt %-20 wt % of pomegranate extract; 1 wt %-20 wt % of yeast beta-glycan; and 1 wt %-20 wt % of soya bean extract, based on the total weight of the herbal composition, respectively.

In one particular example of the invention, the herbal composition of the invention is a product of Virofree provided with Global Preventive Medicine Biotech Co. Ltd (in Taiwan) and/or Geninova Biotech Co., Ltd (in U.S.A.), which comprises about 250 mg grape seed extract, about 180 mg acerola cherry extract, about 160 mg olive leaf extract, about 90 mg marigold extract, about 80 mg green tea extract; 80 mg pomegranate extract; about 80 mg yeast beta-glycan; and about 80 mg soya bean extract, based on the total weight (1000 mg) of the product Virofree, respectively.

In one preferred example of the invention, the herbal composition of the invention consists of about 25% grape seed extract, about 18% acerola cherry extract, about 16% olive leaf extract, about 9% marigold extract, about 8% green tea extract; about 8% pomegranate extract; about 8% yeast beta-glycan; and about 8% soya bean extract, based on the total weight of the composition.

In the present invention, the herbal composition of the invention can be formulated in a commonly used or standard method, to obtain a common pharmaceutical dosage form, including pill, tablet, capsule, drink, or syrup, in combination with a pharmaceutically acceptable carrier.

Another example of the present invention, the herbal composition (Virofree) can be prepared in a dietary form including tablets, capsules, gummies, powders, drink and an energy bar.

In a further aspect, the invention provides a use of the herbal composition according to the invention for manufacturing a supplement or a composition or a pharmaceutical composition for treating or preventing COVID-19 and long COVID The invention will be further described by way of the following examples. However, it should be understood that the following examples are solely intended for the purpose of illustration and should not be construed as limiting the disclosure in practice.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred.

In the drawings.

DETAILED DESCRIPTION OF THE INVENTION

Figure 1:
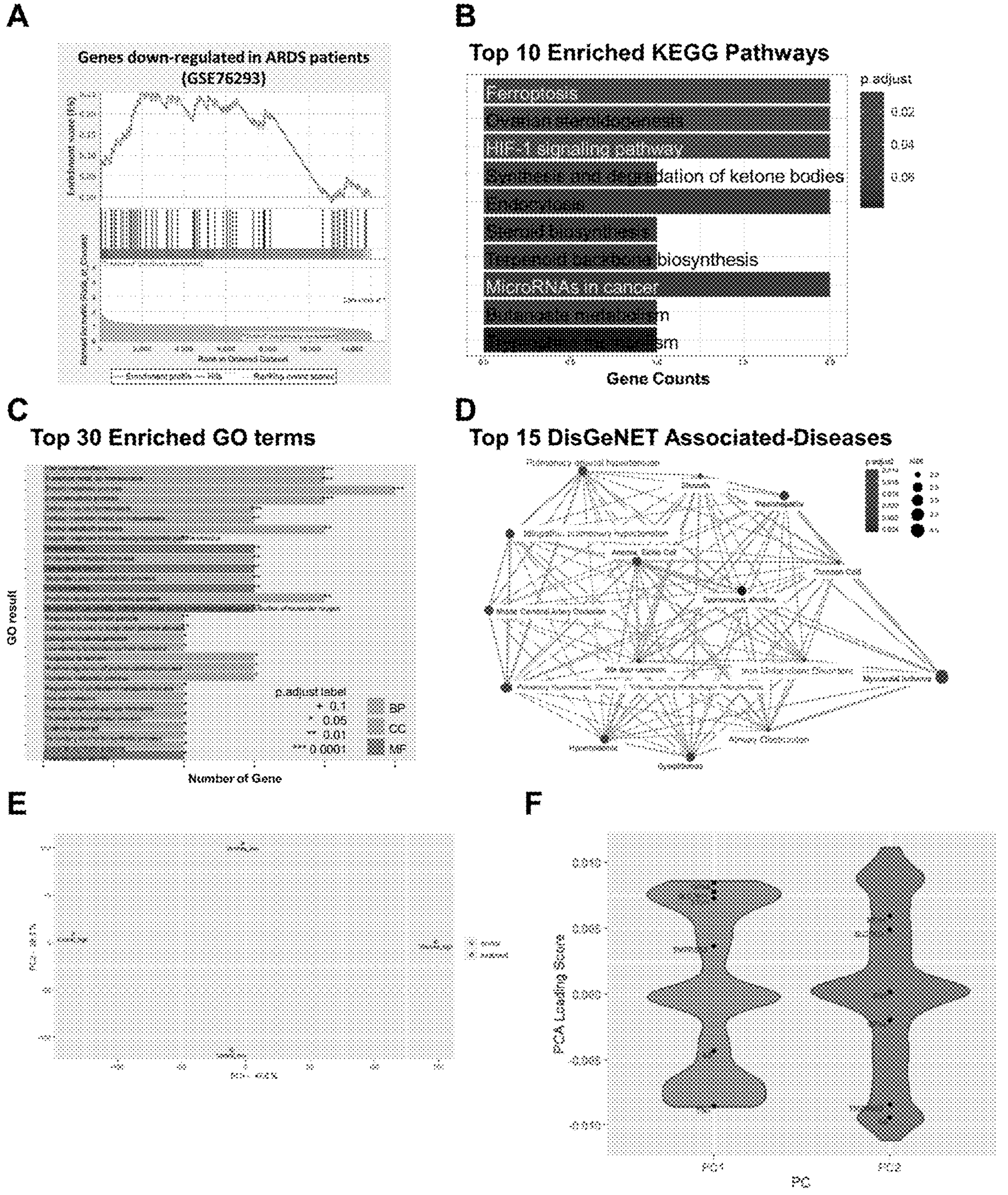
FIG. 1 shows the bioinformatics analysis to identify the underlying mechanism of action of the herbal composition of the invention (i.e., "Virofree") n the treatment of COVID-19; wherein (A) GSEA enrichment plot of gene sets including significantly downregulated genes (log 2FC<−1.5, adjusted p-value<0.05) in Patients with ARDS; a negative enrichment score (NES) implies an enrichment in the downregulated genes by drug treatment; (B-D) shows the bioinformatic analytics for low-dose (66.67 μg/ml) transcriptome profiles of Virofree in BEAS-2B cells; (B) Top 10 pathways from KEGG enrichment analysis of the DEGs; the color intensity denotes the p-value, and the length of the bar indicates the overlapped genes ratio (gene counts) between the input DEGs and the gene set; (C) top 30 Gene Ontology (GO) term enrichmentl the color indicates the term categories including Biological Process (BP), Cellular Component (CC), and Molecular Function (MF)l and the length of the bar indicates the overlapped genes number between the DEGs and GO terms; (D) Associated diseases predicted by the DisGeNET/DO databases; the network illustrated the association among the top 15 diseases, in which the red color highlights the symptoms associated with COVID-19; the statistical results were listed in Table 3 and 4. (E-F) PCA analysis on transcriptomic profiles of low and high doses of Virofree treatment; (E) PCA plot of the on transcriptomic profiles of low and high doses of Virofree treatment; the gene expression profiles were pre-processed to eliminate the batch effect before PCA analysis; (F) loading scores of genes contributing to each principal component (PCs): positive loading scores indicate a positive correlation between the gene expression and the PC; and negative loading scores indicate a negative correlation between the gene expression and the PC.

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

The present invention provides a method and a composition for preventing or treating Covid-19 (an infection of SARS-CoV-2) and long Covid in a subject comprising administering to said subject a therapeutically effective amount of a composition comprising a mixture of grape seed extract, acerola cherry extract, olive leaf extract, marigold extract, green tea extract, pomegranate extract, yeast beta-glucan and soya bean extract.

The term "long COVID" refers to a condition characterized by long-term consequences persisting after the typical convalescence period of COVID-19. It is also known as post-COVID-19 syndrome, post-COVID-19 condition, post-acute sequelae of COVID-19 (PASC), or chronic COVID syndrome (CCS), long COVID can affect nearly every organ system, with sequelae including respiratory system disorders, nervous system and neurocognitive disorders, mental health disorders, metabolic disorders, cardiovascular disorders, gastrointestinal disorders, musculoskeletal pain, and anemia. A wide range of symptoms include fataique, malaise, headaches, shortness of breath, anosmia (loss of smell), parosmia (distorted smell), muscle weakness, low fever and cognitive dysfunction. The exact nature of symptoms and the number of people who experience long-term symptoms are unknown.

In the invention, the bioinformatics analysis platform was proposed drugs capable of inhibiting this disease through multiple biological functions, including virus replication, cytokine storm, and ARDS. By scanning 1.2 thousand-compound profile in the database [11], the herbal composition ("Virofree") was analyzed to discover complete blockers of the pathological mechanism of COVID-19. It was confirmed in the invention that Virofree is a promising for reversing SARS-CoV-2 infection signatures through Gene Set Enrichment Analysis (GSEA) [12]. Based on the clinical observation in the invention, Virofree was confirmed to have the pharmacological properties including prevention and treatment of influenza, secondary treatment for radiotherapy/chemotherapy, reduction in the frequency of asthma attacks, anti-inflammation, tumor cell apoptosis activation, inhibition of cancer metastasis, damaged gene repair. Furthermore, the biological pathways of Virofree were analyzed through another big data system which is the integration of the databases (KEGG [16], Gene Ontology (GO) [17], and Disease Ontology (DO) [18, 19]). It was strongly ascertained in the invention that the Virofree is in connection among ferroptosis, cytokine, miRNA, and ARDS, these mechanisms of action have been frequently reported with COVID-19. Therefore, Virofree is evidenced in the invention to be able to mediate various pathological signals induced by SARS-CoV-2 and provide a comprehensive inhibition to alleviate patients' syndromes after the infection of COVID-19.

It was ascertained that Virofree is a therapeutic composition that can regulate cytokine secretion and impact other targeting pathways to comprehensively interrupt viral infection. Another target was miRNAs, which played key modulators in the cellular process. According to reports by Gonzalo et al., [20] and Kedzierski et al., [21], two teams detected miRNA expression lists in hospitalized COVID-19 patients. There are four common miRNAs in both investigations that regulated the inflammatory response (miR-150-5p, miR-148a-3p) and viral infection (miR-92a-3p, miR-491-5p). Based on previous studies, let-7a and miR-148b were predicted to target the SARS-CoV-2 genome in various regions [22]. The viral replication can also be inhibited by suppresing the activity of viral $M^{pro}$ which can cleave two overlapping polyprotein (pp) 1a and pplab on open reading frame (ORF) 1 to promote more positive-stranded genomic RNA.

Since the viral replication process requires iron [40], macrophages take up the iron to decrease viral iron bioavailability to inhibit viral replication [41]. However, excessive iron accumulation in macrophages leads to the potential for oxidatively damaged phospholipids, eventually triggering a specific form of programmed cell death termed ferroptosis [42]. Cystine/glutamate antiporter xCT and glutathione peroxidase 4 (GPX4) mediates cellular mechanisms against ferroptosis for glutathione biosynthesis and antioxidant defense [43]. It is indicated that understanding and targeting macrophages may help increase the efficacy of COVID-19 treatment. The above description improves the correlation between iron metabolism, the immune system, and ARDS. The last hypothesis function of Virofree altered the stability of iron metabolism and led to the inhibition of the inflammatory response to treat ARDS in COVID-19.

According to the present invention, a promising way is provided to prevent and treat COVID-19 (an infection of SARS-CoV-2) by disrupting the binding and fusion between the viral spike and host ACE2 receptor.

Since the viral replication process requires iron [40], macrophages take up the iron to decrease viral iron bioavailability to inhibit viral replication [41]. However, excessive iron accumulation in macrophages leads to the potential for oxidatively damaged phospholipids, eventually triggering a specific form of programmed cell death termed ferroptosis [42]. Cystine/glutamate antiporter xCT and glutathione peroxidase 4 (GPX4) mediates cellular mechanisms against ferroptosis for glutathione biosynthesis and antioxidant defense [43]. It is indicated that understanding and targeting macrophages may help increase the efficacy of COVID-19 treatment. The above description improves the correlation between iron metabolism, the immune system, and ARDS. The last hypothesis function of Virofree altered the stability of iron metabolism and led to the inhibition of the inflammatory response to treat ARDS in COVID-19.

It was confirmed by an in silico analysis that the herbal composition of the invention, known as "Virofree," reversed the genetic signature of COVID-19 and ARDS.

In the examples of the invention, the biochemical validations showed that Virofree could disrupt the binding of wild-type and Delta-variant spike proteins and ACE2 and its syncytial formation via cell-based pseudo-typed viral assays, as well as suppress binding between several variant recombinant spikes to ACE2, especially Delta and Omicron.

Additionally, it was confirmed in the invention that Virofree elevated miR-148b-5p levels, inhibited the main protease of SARS-CoV-2 ($M^{pro}$), and reduced LPS-induced TNF-α release.

The present invention also prevents the cellular iron accumulation leading to ferroptosis which occurs in SARS-CoV-2 patients. Furthermore, the Virofree in the present invention was able to reduce pulmonary fibrosis-related proteins expression levels in vitro.

In addition, the present invention provides a herbal composition to combat COVID-19 which highlights the inhibitory effect of Virofree on the entry of Delta and Omicron variant of SARS-CoV-2.

The herbal composition may be formulated using any standard technology or commonly used methods known to those skilled in the art.

For the preparation of the concentrate according to the invention, the components are mixed together using the conventional method or any standard method commonly used in the art. In one example, powdered raw materials of the components are mixed to obtain a homogeneous mixture. For the preservation purpose, the concentrate can be pasteurized or lyophilized.

The hearbal composition according to the invention can be in the form of liquid or dried form available. The hearbal composition according to the invention can in the usual way to capsules, tablets, granules or powders are processed. In one example of the invention, the herbal composition is prepared as capsules, which may be obtained by the method of the steps of mixing the components in the form of powder to obtain a mixture and then having the mixture encapsulated.

In another example of the invention, the herbal composition can be formulated or prepared as a beverage, or the concentrates by dissolution of a powder, a tablet or granules in water, cold or hot drinks such as fruit juices or teas.

The present invention will now be described more specifically with reference to the following examples, which are provided for the purpose of demonstration rather than limitation.

EXAMPLES

Example 1: Preparation of Virofree

Virofree, supplied by Geninova Biotech Inc., essentially consists of 250 mg grape seed extract, 180 mg Acerola cherry extract, 160 mg Olive leaf extract, 90 mg Marigold extract, 80 mg Green tea extract, 80 mg Pomegranate extract, 80 mg Yeast beta-glucan, 80 mg Soya bean extract, based on the total weight (1000 mg) of the medicine. The active ingredients are isolated from plant extracts, including Quercetin, Hesperidin, Genistein, Daidzein, and Resveratrol. The medicine is prepared in capsule forms, which is obtained by the method of mixing the components in powder form to obtain a mixture and then encapsulating the mixture.

Example 2

Methods

1. Cell Culture

THP-1, a non-adherent human monocytic cell line derived from an acute monocytic leukemia patient (ATCC, #TIB-202), was purchased from the Bioresource Collection and Research Center and cultured at Roswell Park Memorial Institute (RPMI), (Gibco) 1640 supplemented with 10 mM HEPES, 10% fetal bovine serum (FBS), 1% penicillin-streptomycin, and 50 μM β-mercaptoethanol, and held in the Petri dish in a 5% carbon dioxide-humidified atmosphere at 37° C. Cells were passaged continuously after 3-4 days. For the experiment, the cell line was used before passage 8.

BEAS-2B, a human normal bronchial epithelial cell line (ATCC, #CRL-9609), was cultured in RPMI medium supplemented with 10% FBS (Invitrogen), 1% PSA, 1% nonessential amino acid, and 2 mM L-glutamate (Invitrogen). Cells were maintained at 37° C. with 5% $CO_2$ in a cell incubator and passaged every 3-4 days. For the experiment, the cell line was used at early passage (before passage 6).

LL29, a human lung fibroblast cell line derived from idiopathic pulmonary fibrosis lung tissue (ATCC, #CCL-134). LL29 cells were cultured in Ham's F12K medium with 15% FBS (Invitrogen) and 1% PSA. Cells were cultured at 37° C. in a 5% $CO_2$ atmosphere and trypsinized every 3-4 days. For the experiment, the cell line was used at early passage (before passage 8).

Baby hamster kidney (BHK)-21 cells, a fibroblast cell line derived from baby hamster kidneys (ATCC, #CCL-10), and Calu-3 cells, a human epithelial lung cell line derived from a patient with lung adenocarcinoma (ATCC, #HTB-55), were cultured in Dulbecco's Modified Eagle Medium (DMEM, Gibco) supplemented with 10% FBS and 1×penicillin/streptomycin solution. BHK-21 and Calu-3 cells were incubated at 37° C. in a 5% $CO_2$ atmosphere and trypsinized every 2 days and 3-4 days, respectively. For the experiment, the cell line was used at early passage (before passage 8).

2. Sulforhodamine B Colorimetric Assay

The sulforhodamine B (SRB) assay is used for cell density determination based on the measurement of cellular protein content. The method described here has been optimized for compounds toxicity screening for adherent cells in a 96-well plate. Cells were seeded at 2,000 cells per well for 16-20 h and then treated with different concentrations of different drugs for 24 h. The medium was discarded, and the cells were gently washed twice with phosphate-buffered saline (PBS) and fixed with cold 10% trichloracetic acid (w/v) (SIGMA) at 4° C. for 1 h. After fixation, plates were washed twice with water and air-dried. Cells were stained with 100 μl/well of 0.1% (w/v, in 1% acetic acid) SRB solution at room temperature for 1 h, and then washed twice with 1% acetic acid (AVANTOR). After air drying, 100 μl of 20 mM Tris-base was added to each well and read at optical density (OD) 540 nm.

3. Quantitative Reverse Transcription Polymerase Chain Reaction (PCR) Analysis

BEAS-2B cells derived from human normal bronchial epithelium were used to detect biological agents affecting infection mechanisms in the respiratory tract. To evaluate the effect of Virofree on let-7a and miR-148 expression, 1×106 BEAS-2B cells were seeded in a 10-cm dish 24 h before drug treatment. Cells were then collected after 24 h of treatment. TRIzol® reagent was used for total RNA extraction, and RNA samples were stored at −80° C. The miRNA levels of let-7a and miR-148b expression were quantified using quantitative reverse transcription PCR (qRT—PCR) with U54 as an internal control. Real time-PCR primers were used for amplification, including forward sequences specific for hsa-let-7a-5p (5'-GCCTGAGGTAGTAGGTTGTATAGTTA-3'), hsa-miR148b-5p (5'-AAGUUCUGUUAUACACUCAGGC-3'), and U54 (homo) (5'-GGTACCTATTGTGTTGAGTAACGGTGA-3'). qRT—PCR was performed using Phalanx miRNA One Array® Profiling (Phalanx Biotech Group).

4. Cytokine Determination Assay

The THP-1 cell line was used as a cell model. THP-1 cells were differentiated by 50 ng/ml of phorbol 12-myristate 13-acetate (PMA) (SIGMA; P1585) for 24 h. After washing non-adherent cells with RPMI-free serum, 100 ng/ml of lipopolysaccharide (LPS) (SIGMA; L2654) was used as a stimulator to mimic the inflammatory condition, and treatment of LPS 100 ng/ml alone in differentiated THP-1 cells was considered as the positive control. The cells were treated with the drug with or without the presence of LPS and incubated at 37° C. for 6 or 24 h. The cell medium was then collected and stored at −20° C. The level of TNF-α released by treated cells was detected using an enzyme-linked immunosorbent assay (ELISA) assay. The supernatants were analyzed in Nunc MaxiSorp® flat-bottom 96-well plates (Invitrogen, ThermoFisher; #442402) using a human TNF-α uncoated ELISA kit following the manufacturer's protocol (Invitrogen, Thermofisher; #88-7346). The OD value was measured with the Infinite 200Pro OD reader, using the Tecan i-control program at 450 nm and 570 nm wavelengths.

5. Inhibition of $M^{pro}$ Activity and Determination of the Half-Maximal Inhibitory Concentration ($IC_{50}$)

To determine Mpro activity inhibition ability, Virofree was used as an inhibitor in an enzyme-substrate assay in which Mpro was cleaved at the cleavage site of the fluorogenic peptide substrate (Abz-TSAVLQSGFRK-Dnp) in PBS. Virofree was incubated at 30° C. for 3 min together with a fluorogenic peptide substrate in PBS, followed by protease addition and equilibrated at 30° C. for 3 min. The fluorescence emission at 423 nm was detected by excitation at 321 nm using a luminescence spectrometer (PerkinElmer LS50B) [24]. The IC50 value was obtained from the following equation $$v = \frac{v_0}{(1 + IC_{50}^n)/[I]^n}$$

where v is the velocity at different concentrations of the incubated inhibitor [I], and v0 is the initial velocity without inhibitor incubation, whereas n is the Hill constant.

6. Cell-Cell Fusion

Human lung cancer Calu-3 cells, used as recipient cells, were first seeded in a 12-well plate at 1×106 cells per well to form a single layer of cells. BHK-21 cells were seeded at 4×105 cells per well in a 6-well plate and transfected with EGFP and spike plasmids (the original Wuhan strain or Delta variant) at a ratio of 1:5 using Lipofectamine2000. After 24 h, EGFP-Spike BHK cells were harvested by adding 1 ml of cell dissociation buffer (5 mM EDTA in PBS) into each well to detach intact cells and resuspended in serum-free DMEM (Gibco). Transfected BHK-21 cells expressing both EGFP and spike genes were used as donor cells; were co-cultured in a single layer of Calu-3 cells, used as target cells, for cell-cell contact in the presence or absence of Virofree treatments and incubated at 4° C. for 1 h. After 1 h, PBS was used to wash away unbound cells and replaced with a growth medium. Initial images of EGFP-positive cells, representing the binding efficiency, were acquired in five random fields using an inverted fluorescence microscope (Olympus IX70). The binding efficiency of EGFP-positive BHK-21 cells with Calu-3 cells in the control and Virofree-treated groups was quantified by counting the initial number of EGFP-positive BHK-21 cells attached to Calu-3 cells. The number of EGFP cells in the control group was defined as having a binding efficiency of 100%. Therefore, the effect of Virofree on binding efficiency was determined by the percentage of binding efficiency normalized to control. These cells were then treated with the corresponding treatments and then incubated at 37° C. for an additional 4 h for wild-type or 2 h for Delta variant, and then randomly selected images of five fields of EGFP-positive cells were acquired to evaluate the fusion efficiency. Syncytial cells formation was calculated by quantifying the expansion area of EGFP-positive cells in these images using ImageJ. The fold change in the EGFP-positive area in the control group from initial to 4 h (wild-type) or 2 h (Delta) was considered as 100% fusion efficiency. The effect of Virofree on syncytia formation was calculated according to the following equation:

$$\text{The normalized percentage (\%)} = \frac{\text{the fold change of GFP area}}{\text{the fold change of GFP area in control}} \times 100$$

7. Pseudo-Typed Virus Neutralization Assay

Neutralization assays were performed by incubating wild-type (G-SARS-CoV2-Pseudovirus WT, LumiSTAR), delta (G-SARS-CoV2-Pseudovirus, B.1.617.2, LumiSTAR) or omicron pseudoviruses (G-SARS-CoV2-Pseudovirus, B.1.1.529, LumiSTAR) with serial dilutions of compounds at the desired concentration in Opti-MEM. HEK-293T cells (1×104) stably expressing human ACE2 genes were seeded in 50 μL of Opti-MEM (Gibco) in each well of a black μCLEAR flat-bottom 96-well plate (Greiner Bio-one™) and cells were incubated overnight at 37° C. with 5% CO2. The next day, each compound was serially diluted three-fold in Opti-MEM and incubated with SARS-CoV-2 pseudo-typed lentivirus at 37° C. for 1 h. The tested drug was diluted three times until the lowest concentration was 1 μg/ml. The virus-compound mixture was transferred to the 293T/ACE2 cell plate with a final multiplicity of infection of 0.1. The culture medium was then replaced with fresh DMEM (supplemented with 10% FBS, 100 U/ml penicillin/streptomycin) at 16 h post-infection and cells were cultured continuously for another 56 h. After incubating the infected cells at 37° C. for 72 h, the GFP fluorescence in the cells was quantified in the ImageXpress Micro Confocal High-Content Imaging System (Molecular Devices).

8. Image and IC50 Fitting

After incubation at 37° C. for 72 h, infected cells were stained with DAPI at 37° C. for 20 min. Then GFP-positive cells and total cell nuclei were detected using an ImageXpress Micro Confocal High-Content Imaging System (Molecular Devices). Raw images (5×5 sites, total 25 sites) were acquired using a 20×water immersion objective lens, following by processing and stitching using the appropriate settings. Total cells (indicated by nucleus staining) and GFP-positive cells were quantified for each well. All analyses were carried out using the MetaXpress Cell Scoring module, counting positive cells and the total cell numbers at each site. After Cell Scoring analysis, the raw data were processed by Lumi-Vcal (LumiSTAR custom analysis software). Transduction rates were determined by dividing the GFP-positive cell by the total cell number. Relative transduction rates were obtained by normalizing the infection rates of the drug-treated groups to those of the PBS-treated controls. The inhibition percentage was obtained based on the assumption that the PBS-treated control induced 0% inhibition. The curves of relative inhibition rates versus drug concentration were plotted using Prism 8 (GraphPad). A nonlinear regression method [25] was used to determine the drug concentration at which 50% of GFP (IC50) was expressed. Each drug was tested in triplicate. All SARS-CoV-2 pseudovirus neutralization assays were performed at a BSL-2 facility.

9. Enzyme-Linked Immunosorbent Assay

An additional experiment was performed using ELISA to evaluate the efficacy of Virofree in interfering with the binding of trimeric SARS-CoV-2 spike protein wild-type (Wuhan strain) or variants (α, β, γ, δ, o) and δ variant of the SARS-CoV-2 spike protein RBD domain to biotinylated human ACE2 recombinant protein. Firstly, each well of a 96-well plate was coated with 100 μl of spike protein (500 ng/ml; cat. GTX135972-pro, GeneTex, Taipei, Taiwan) diluted in coating buffer, consisting of sodium carbonate (15 mM), sodium hydrogen carbonate (35 mM), pH 9.6, at 4° C. overnight. The coated plate was then washed thrice with washing buffer consisting of PBS with 0.05% (v/v) Tween-20 (pH 7.4) and subsequently blocked with 250 μl of blocking buffer consisting of 0.5% (w/v) bovine serum albumin for 1.5 h at 37° C. The plate was washed thrice, then 100 μl of tested drug or inhibitor (10 μg/ml; cat. GTX635791, GeneTex, Taipei, Taiwan) in dilution buffer was added to the plate and incubated for 1 h at 37° C. 100 μl of biotinylated human ACE2 protein (10 ng/ml; cat. AC2-H82E6; ACRO Biosystems, OX, UK) was added to each well and incubated for another 1 h at 37° C. The binding of spike protein and ACE2 receptor without drug or inhibitor was considered as positive control. The plate was then washed thrice with wash buffer before adding 100 μl of Streptavidin-HRP conjugate (100 ng/ml; cat. GTX30949, GeneTex, Taipei, Taiwan) in dilution buffer was added and incubating for 1 h at 37° C. The plate was then washed and incubated with 200 μl of TMB substrate per well for 20 min at 37° C. under light protection. Subsequently, 50 μl of stop solution was added to terminate the reaction, and the absorbance at 450 nm was detected using a microplate reader (Cytation 5, BioTek, Vermont, USA)

10. Western Blot Analysis

The cells were exposed to different treatments for the indicated time, the cells were lysed on ice with lysis buffer. The cell lysate was cleared by centrifugation at 12,000 g for 10 min. The lysate was resolved by sodium dodecyl sulfate-polyacrylamide gel electrophoresis, and the proteins were transferred to a polyvinylidene fluoride membrane. After blocking with 5% non-fat dry milk in Tris-buffered saline, the membrane was incubated overnight with the desired primary antibody (FPN (Novus Biologicals, NBP1-21502, 1:1000), FTH-1 (Cell signaling, 4393S, 1:1000), GPX4 (Abcam, ab125066, 1:1000), TFRC (Cell signaling, 13208s, 1:1000), xCT (Cell signaling, 17681s, 1:1000), GAPDH (GeneTex, GTX100118, 1:10,000), α-SMA (Abcam, ab5694, 1:1000), Fibronectin (Santa Cruz, sc-9068, 1:1000), N-cadherin (BD, 610920, 1:1000), β-actin (GeneTex, GTX109639, 1:10000)). Subsequently, the membrane was incubated with an appropriate secondary antibody. Immunoreactive bands were visualized using the enhanced chemiluminescence (ECL) method and captured by a Luminescence Imaging system (LAS 4000™, Fuji Photo Film Co. Ltd).

11. RNAseq and Data Mining

Figure 8:
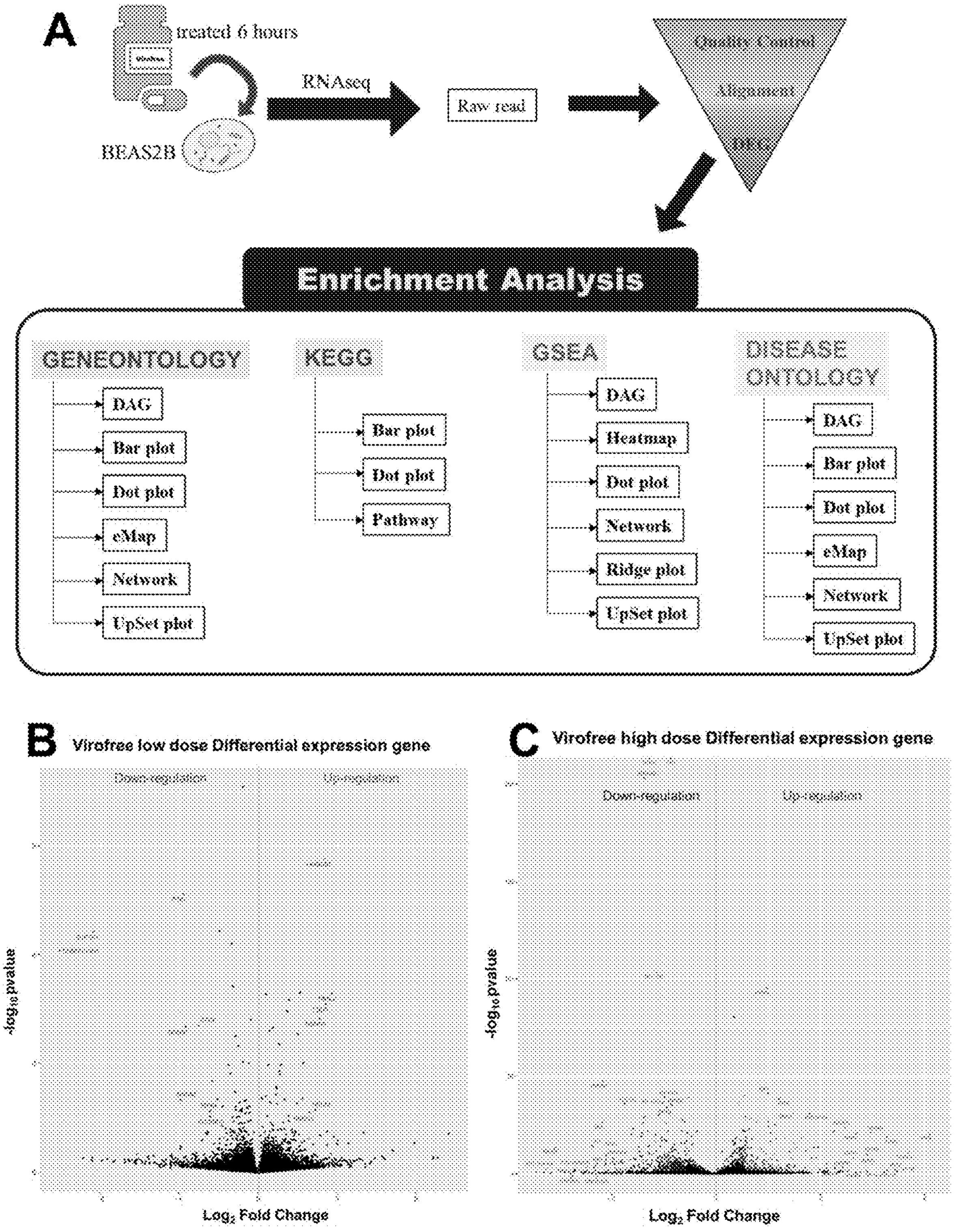
FIG. 8 shows the overview of the analysis pipeline; (A) After 6 h of 66.67 μg/ml or 500 μg/ml of Virofree treatment in BEAS2B, RNA was extracted for next-generation sequencing and the substantial differential expression levels and enrichment analysis were analyzed; the platform, including four databases, Gene Ontology (GO), KEGG, Disease Ontology (DO), and GSEA, can reveal the mechanisms of Virofree through big data analysis. The identification of the significant differential expression genes of Virofree. BEAS-2B cells were treated with 66.67 μg/ml (B) or 500 μg/ml Virofree (C) and RNA was extracted for next-generation sequencing; compared with the control and calculated log 2 fold change (x-axis), the positive/negative values denoted up/downregulation genes were shown as a volcano plot. The y-axis showed the significant change between Virofree and the control. Cut-off denoted 1.5 log 2 fold change; the detailed information is listed in Table 2.

Total RNA from two concentrations of Virofree and the PBS control sample in BEAS-2B cells was extracted with the RNeasy Mini kit (Qiagen). The mRNA expression level of each sample was detected using next-generation sequencing-RNAseq (Biotools Microbiome Research Center Inc.). The bioinformatics pipeline is outlined in FIG. 8. Two different concentrations were used for transcriptomic response profiling, including 66.67 μg/ml (low dose) and 500 μg/ml (high dose). The raw read counts were normalized using “Trimmed Mean of M-values” via edgeR (v3.8.1) [26, 27], and biologically unduplicated differentially expressed gene (DEGs) analysis was performed through DEGseq package (v1.40.0) using MARS (MA-plot-based method with Random Sampling model) method [28].

12. Gene Set Enrichment Analysis

The GSEA is a computational method that determines whether a pre-defined set of genes shows statistically significant differences between two phenotypes (treatment vs. no treatment) [29]. The goal of GSEA is to determine whether members of a gene set tend to appear at the top (or bottom) of the ranked gene list. The ranked list is based on differential gene expression between two phenotypes. GSEA assigns an enrichment score based on the Kolmogorov-Smirnow statistic for each gene set and then normalizes the score based on their size. A positive score indicates gene set enrichment at the top of the ranked list, whereas a negative score indicates gene set enrichment at the bottom of the ranked list. Finally, based on the normalized enrichment score, a permutation-based false discovery rate is generated to indicate the significance of the enrichment score. GSEA was performed using the C2 and C7 gene set collections from the MSigDB v.7.2. COVID-19 and ARDS-related signatures are sets of genes up- or downregulated in disease conditions retrieved from MSigDB and Gene Expression Omnibus (GEO) databases. The GSE76293 microarray retrieved from GEO was analyzed by the limma package. The GSEA analysis was performed using the class ratio for metrics to rank genes, 1000 permutations with gene set permutation types.

13. Principal Component Analysis (PCA)

Gene expression profiles of the two-dose Virofree treatment were adjusted through the sva package to eliminate the batch effect [30]. PCA analysis was performed via prcomp in R.

14. Establishing Bleomycin-Induced ARDS Rat Model

Six-week-old male Sprague-Dawley rats were anesthetized with Zoletil 20-40 mg/kg and Xylazine 5-10 mg/kg (intraperitoneal injection) before administering 5 mg bleomycin/250 g body weight (Nippon Kayaku Co., Ltd.) in 200 μl PBS by intratracheal injection and then placed 60 o to the left side for 90 min. Animals were randomized to the following treatment: (a) BLM group (n=1) rats were injected intratracheally with 5 mg BLM and sacrificed on day 8. From day 1 up to day 7, 0.5 ml of saline was orally administered to the rats twice daily. (b) BLM+Virofree (n=2) rats received intratracheal injection with 5 mg BLM and were sacrificed on day 8. From day 1 to day 7, Virofree with 150 mg/0.5 ml saline was orally administered to the rats twice per day. The dose was decided following animal equivalent dose calculation based on body surface area [31].

16. Statistical Analysis

Data are expressed as mean±SD or SEM. Data were compared to the corresponding control in each experiment by one-way ANOVA, followed by Dunnett’s post-test using Prism 8 (GraphPad). A p-value of <0.05 was considered statistically significant.

Results:

1. Gene Set Enrichment Analysis Reveals the Reversed Signature of COVID-19 Induced by Virofree.

To screen for COVID-19 candidate treatments, transcriptomic response profiles for different drug treatments were analyzed to determine if a given drug could reverse the disease signature gene sets. Signatures of COVID-19, CRS, and ARDS are characterized by genes that are up- or down-regulated in disease conditions, and reversed signatures refer to genes increased/decreased in disease conditions that may be decreased/increased with drug treatment.

The COVID-19 signature was described by Blanco-Melo et al. [32] as one involving greater up- or down-regulation of genes induced by SARS-CoV-2 infection as compared with other respiratory viruses, indicating a unique signature of COVID-19. These gene sets were integrated into the MSigDB database for GSEA analysis. The results suggest that Virofree treatment can reverse the SARS-CoV-2 infection signature in A549 cells, in which genes up-regulated by SARS-CoV-2 infection were downregulated (normalized enrichment score (NES)<0) and downregulated genes were elevated (NES>0) by the treatment (Table 1). Furthermore, it appears that the present invention had more effect on cells expressing ACE2.

TABLE 1

Enrichment analysis of Virofree treatment transcriptomic profiles in gene sets related to COVID-19 pathology.

| | Gene set name | NES | NOM p-val | FDR q-val | MSigDB systematic name |
|---|---|---|---|---|---|
| SARS-CoV2 infection gene sets | Genes down-regulated in SARS-CoV-2 infection in A549 cells | 2.25 | 0.00 | 0.02 | M34011 |
| | Genes down-regulated in SARS-CoV-2 infection with Ruxolitinib in ACE2 expressing A549 cells | 2.19 | 0.00 | 0.02 | M34019 |

TABLE 1-continued

Enrichment analysis of Virofree treatment transcriptomic profiles in gene sets related to COVID-19 pathology.

| | Gene set name | NES | NOM p-val | FDR q-val | MSigDB systematic name |
|---|---|---|---|---|---|
| | Genes down-regulated in SARS-CoV-2 infection on ACE2 expressing A549 cells | 1.97 | 0.00 | 0.07 | M34017 |
| | Genes down-regulated in SARS-CoV-2 infection in bronchial epithelial cells | 1.73 | 0.02 | <0.25 | M34021 |
| | Genes up-regulated in SARS-CoV-2 low MOI infection in ACE2 expressing A549 cells | −2.06 | 0.00 | 0.03 | M34014 |
| | Genes up-regulated in SARS-CoV-2 infection with Ruxolitinib in ACE2 expressing A549 cells | −1.85 | 0.00 | 0.05 | M34618 |
| CRS gene sets | Genes up-regulated in CD4 T cells treated with TGF beta and IL6 | −2.41 | 0.00 | 0.003 | M7467 |
| | Genes down-regulated on treatment of normal human bronchial epithelial cells with beta interferon | 1.62 | 0.04 | <0.25 | M34023 |
| ARDS gene sets | Genes down-regulated in ARDS patients | 1.87 | 0.01 | 0.01 | |

CRS: Cytokine release syndrome, as known as cytokine storm

GSEA analysis also indicated the effect of Virofree in reducing CRS. There was a decrease of IL-6 signaling in $CD4^+$ T cells (NES=−2.41, q-value=0.003) and an increase in the genes downregulated by interferon-β treatment in bronchial epithelial cells (NES=1.62, q-value<0.25), indicating a decreased IL-6 and an increased interferon-β secretion by Virofree treatment (Table 1). The effect of Virofree on ARDS was also examined by GSEA analysis using the ARDS signature. The ARDS signature was achieved by significantly up/downregulated genes in blood polymorphonuclear neutrophils (PMNs) from patients with ARDS (GSE76293). A positive NES (NES=1.87, q-value=0.01) indicated that Virofree could enhance downregulated genes in patients with ARDS (Table 1, FIG. 1A). The GSEA analysis suggests that Virofree could reverse COVID-19 signatures by reducing CRS through inhibition of IL-6 and activation of an interferon-β signaling pathway to reduce ARDS-associated COVID-19.

2. The Big Data Analysis Implies that Ferroptosis and miRNA are Virofree Potential Targets for COVID-19 Treatment.

The underlying mechanism of action of Virofree can be revealed through drug treatment gene expression profiling. Transcriptional responses to treatment have profiled the low dose (66.67 μg/ml) of Virofree treatment in BEAS-2B cells. There were 6 up-regulation genes and 8 downregulation genes resulting from the low-dose Virofree treatment (Table 2). KEGG enrichment revealed that Virofree functions are related to ferroptosis, HIF-1 signaling pathway, steroid metabolism, and miRNA in cancer (FIG. 1B). In addition, GO showed the 30 major biological pathways that mediated iron-ion homeostasis, sterol metabolism process, virus receptor activity, and clathrin-coated pit (FIG. 1C). Virofree transcriptomic response profiles were connected to disease signatures via the DisGeNET database, in which the top 10 associated diseases included iron metabolism disorders, airway obstruction, pulmonary arterial hypertension, and idiopathic pulmonary hypertension (FIG. 1D). The high Virofree dose (500 μg/ml) demonstrated microRNA regulation from the GO results (FIG. 9A) whereas the KEGG bar plot showed that treatment was associated with response to the transforming growth factor-beta and response to oxygen levels (FIG. 9B). Generally, it suggested that Virofree mediated cellular iron-ion homeostasis, miRNA, and viral infection signaling to inhibit COVID-19 symptoms.

TABLE 2

Significant up and downregulated genes of high and low-dose Virofree treatment response profiles. Low dose (66.67 μg/ml) showed 6 up and 8 down of significant differential expression genes. The top 10 DEGs of high dose (500 μg/ml) are listed in the table.

| | Virofree 66.67 μg/ml (low dose) | | | Virofree 500 μg/ml (high dose) | | |
|---|---|---|---|---|---|---|
| Treatment DEG | Gene | log2 Fold Change | p-value | Gene | log2 Fold Change | p-value |
| Up | HMGCS1 | 8.29E−01 | 2.23E−09 | HSPA5 | 9.72E−01 | 1.99E−95 |
| | FBXL5 | 9.31E−01 | 1.25E−05 | EIF1 | 9.91E−01 | 7.01E−42 |
| | LDLR | 8.50E−01 | 2.45E−05 | ATF4 | 1.21E+00 | 3.85E−39 |
| | MSMO1 | 7.81E−01 | 6.10E−05 | RND3 | 1.48E+00 | 3.43E−32 |
| | HMOX1 | 6.47E−01 | 2.18E−02 | PPP1R15A | 1.78E+00 | 1.33E−31 |
| | HELZ2 | 7.23E−01 | 1.87E−02 | RP518 | 6.52E−01 | 4.19E−29 |
| | | | | SRSF6 | 9.93E−01 | 7.66E−28 |
| | | | | UBC | 7.86E−01 | 2.41E−27 |
| | | | | CXCL8 | 1.13E+00 | 6.23E−26 |
| | | | | STC2 | 1.00E+00 | 4.88E−25 |

TABLE 2-continued

Significant up and downregulated genes of high and low-dose Virofree treatment response profiles. Low dose (66.67 μg/ml) showed 6 up and 8 down of significant differential expression genes. The top 10 DEGs of high dose (500 μg/ml) are listed in the table.

| | Virofree 66.67 μg/ml (low dose) | | | Virofree 500 μg/ml (high dose) | | |
|---|---|---|---|---|---|---|
| Treatment DEG | Gene | log2 Fold Change | p-value | Gene | log2 Fold Change | p-value |
| Down | TFRC | −9.40E−01 | 2.08E−08 | FN1 | −8.63E−01 | 0.00E+00 |
| | CYP1B1 | −2.09E+00 | 2.29E−07 | THBS1 | −1.29E+00 | 0.00E+00 |
| | CH507-513H4 | −2.52E+00 | 8.01E−07 | SERPINE1 | −1.37E+00 | 5.58E−204 |
| | STC2 | −7.51E−01 | 9.12E−05 | MT-CO1 | −1.12E+00 | 4.32E−104 |
| | TIPARP | −9.23E−01 | 1.00E−04 | PMEPA1 | −2.16E+00 | 4.01E−48 |
| | SLC25A37 | −6.07E−01 | 2.84E−02 | MT-ND5 | −9.79E−01 | 3.57E−40 |
| | SHISA2 | −9.79E−01 | 1.00E−02 | MT-CO3 | −1.02E+00 | 2.62E−37 |
| | RIPK4 | −6.09E−01 | 2.02E−02 | COL1A1 | −1.75E+00 | 1.35E−36 |
| | | | | PRKDC | −8.60E−01 | 4.15E−36 |
| | | | | MK167 | −9.34E−01 | 1.04E−34 |

DEG: differential expression gene.

Treatments of two different doses of Virofree have been compared by their effects on gene expression levels and associated diseases. (Table 3 and Table 4)2 DEGs were up-regulated and 4 DEGs were downregulated at both drug concentrations; however, STC2 was the only gene with a significant change in expression levels when the dosage of Virofree was increased (FIG. 9C). About 700 genes were induced or inhibited by the higher dose of Virofree, and these DEGs did not show at the lower dose of Virofree, meaning there was no difference between control and treatment. 5 common associated diseases can be interfered with by low and high doses of Virofree, which are pulmonary arterial hypertension, myocardial ischemia, pulmonary hypertension (primary, 1, with hereditary hemorrhagic telangiectasia), idiopathic pulmonary hypertension, and steatohepatitis, respectively (FIG. 9D).

TABLE 3

The detailed list of prediction pathways and diseases of low-dose Virofree from multi-databases
Virofree 66.67 μg/ml (low dose)

| Pathway description | p-value | Overlapped gene symbol |
|---|---|---|
| Top 10 Enriched KEGG database | | |
| Ferroptosis | 3.73E−04 | TFRC/HMOX1 |
| Ovarian steroidogenesis | 5.78E−04 | CYP1B1/LDLR |
| HIF-1 signaling pathway | 2.62E−03 | TFRC/HOMX1 |
| Synthesis and degradation of ketone bodies | 7.41E−03 | HMGCS1 |
| Endocytosis | 1.30E−02 | TFRC/LDLR |
| Steroid biosynthesis | 1.48E−02 | MSMO1 |
| Terpenoid backbone biosynthesis | 1.62E−02 | HMGCS1 |
| MicroRNAs in cancer | 1.99E−02 | CYP1B1/HMOX1 |
| Butanoate metabolism | 2.06E−02 | HMGCS1 |
| Tryptophan metabolism | 3.08E−02 | CYP1B1 |
| Top 30 Enriched GO database | | |
| Iron ion homeostasis | 1.08E−07 | TFRC/FBXL5/HMOX1/SLC25A37 |
| Transition metal ion homeostasis | 9.26E−07 | TFRC/FBXL5/HMOX1/SLC25A37 |
| Steroid metabolic process | 1.35E−06 | HMGCS1/CYP1B1/LDLR/MSMO1/TIOARP |
| Sterol metabolic process | 2.67E−06 | HMGCS1/CYP1B1/MSMO1 |
| Cellular iron ion homeostasis | 5.58E−06 | TFRC/FBXL5/HMOX1 |
| Cellular transition metal ion homeostasis | 3.49E−05 | TFRC/FBXL5/HMOX1 |
| Alcohol metabolic process | 6.37E−05 | HMGCS1/CYP1B1/LDLR/MSMO1 |
| Cellular response to low-density lipoprotein particle stimulus | 7.06E−05 | HMGCS1/LDLR |
| Cholesterol metabolic process | 9.39E−05 | HMGCS1/LDLR/MSMO1 |
| Tetrapyrrole binding | 1.03E−04 | CYP1B1/STC2/HMOX1 |
| Secondary alcohol metabolic process | 1.03E−04 | HMGCS1/LDLR/MSMO1 |
| iron ion binding | 1.11E−04 | CYP1B1/FBXL5/MSMO1 |
| Positive regulation or catabolic process | 1.19E−04 | FBXL5/LDLR/TIPARP/HMOX1 |
| Oxidoreductase activity | 1.27E−04 | CYP1B1/MSMO1/HMOX1 |
| Response to lipoprotein particle | 1.51E−04 | HMGCS1/LDLR |
| Cellular response to lipoprotein particle stimulus | 1.71E−04 | HMGCS1/LDLR |
| Estrogen metabolic process | 2.74E−04 | CYP1B1/TIPARP |
| Low-density lipoprotein particle clearance | 3.01E−04 | LDLR/HMOX1 |
| Response to nutrient | 3.20E−04 | HMGCS1/STC2/HMOX1 |
| Positive regulation of protein catabolic process | 3.56E−04 | FBXL5/LDLR/TIPARP |
| Hormone metabolic process | 4.91E−04 | CYP1B1/STC2/TIPARP |
| Regulation of cholesterol metabolic process | 6.66E−04 | HMGCS1/LDLR |
| Iron ion transport | 8.12E−04 | TFRC/SLC25A37 |
| Plasma lipoprotein particle clearance | 9.02E−04 | LDLR/HMOX1 |

TABLE 3-continued

| The detailed list of prediction pathways and diseases of low-dose Virofree from multi-databases Virofree 66.67 μg/ml (low dose) | | |
|---|---|---|
| Cholesterol biosynthesis process | 9.25E−04 | HMGCS1/MSMO1 |
| Clathrin-coated pit | 9.48E−04 | TFRC/LDLR |
| Secondary alcohol biosynthesis process | 9.48E−04 | HMGCS1/MSMO1 |
| Sterol biosynthetic process | 1.07E−03 | HMGCS1/MSMO1 |
| Virus receptor activity | 1.22E−03 | TFRC/LDLR |
| **Associated-disease description** | **p-value** | **Overlapped gene symbol** |
| Top 15 Enriched DisGeNET database | | |
| Iron Metabolism Disorders | 2.83E−05 | TFRC/HMOX1 |
| Middle Cerebral Artery Occlusion | 6.20E−05 | STC2/HMOX1/SLC25A37 |
| Common Cold | 1.41E−04 | HMOX1/LDLR |
| Stenosis | 2.53E−04 | HMOX1/LDLR |
| Pulmonary arterial hypertension | 2.66E−04 | HMOX1/CYP1B1/SLC25A37 |
| Myocardial Ischemia | 3.26E−04 | TFRC/TIPARP/HMOX1/LDLR |
| Pulmonary Hypertension Primary | 3.34E−04 | HMOX1/CYP1B1/SLC25A37 |
| Bile duct carcinoma | 5.35−04 | HMOX1/CYP1B1/SLC25A37 |
| Idiopathic pulmonary hypertension | 5.35E−04 | HMOX1/CYP1B1/SLC25A37 |
| Steatohepatitis | 5.35E−04 | TIPARP/HMOX1/LDLR |
| Dyslipidemias | 5.78E−04 | HMOX1/LDLR/MSMO1 |
| Airway Obstruction | 5.95E−04 | TFRC/HMOX1 |
| Anemia, Sickle Cell | 6.08E−04 | TFRC/HMOX1/LDLR |
| Hyperlipidemia | 6.08E−04 | HELZ2/HMOX1/LDLR |
| Spontaneous abortion | 7.47E−04 | TFRC/HMOX1/CYP1B1 |

TABLE 4

The detailed list of prediction pathways and diseases of high-dose Virofree from multi-databases. Virofree 500 μg/nl (high dose)

| Pathway description | p-value |
|---|---|
| Top 10 Enriched KEGG database | |
| Small cell lung cancer | 1.12E−09 |
| Focal adhesion | 4.16E−09 |
| Proteoglycans in cancer | 3.38E−07 |
| ECM-receptor interaction | 5.82E−07 |
| Human papillomavirus infection | 2.13E−06 |
| PI3K-Ak1 signaling pathway | 3.96E−06 |
| p53 signaling pathway | 6.37E−06 |
| Melanoma | 2.69E−05 |
| Non-small cell lung cancer | 2.69E−05 |
| MicroRNAs in cancer | 5.85E−05 |
| Top 30 Enriched GO database | |
| Response transforming growth factor beta | 5.35E−15 |
| Cellular response to transforming growth factor beta stimulus | 3.26E−13 |
| Heart morphogenesis | 4.13E−13 |
| Transmembrane receptor protein serine kinase signaling pathway | 1.75E−11 |
| Cell-substrate junction | 2.23E−11 |
| Response to oxygen levels | 3.12E−11 |
| Extracellular matrix organization | 3.36E−11 |
| Artery development | 3.46E−11 |
| Focal adhesion | 4.46E−11 |
| Cell-substrate adherens junction | 5.57E−11 |
| Epithelial cell development | 1.03E−10 |
| Reproductive structure development | 1.23E−10 |
| Regulation of vasculature development | 1.43E−10 |
| Reproductive system development | 1.54E−10 |
| Response to decreased oxygen levels | 2.01E−10 |
| Cell-substrate junction assembly | 3.08E−10 |
| Regulation of Ras protein signal transduction | 3.46E−10 |
| Cardiac chamber development | 3.54E−10 |
| Regulation of small GTPase mediated signal transduction | 3.79E−10 |
| Response to steroid hormone | 6.28E−10 |
| Placenta development | 9.33E−10 |
| Extracellular structure organization | 9.47E−10 |
| Positive regulation of vasculature development | 9.57E−10 |
| Cellular response to external stimulus | 1.22E−09 |
| Cell junction organization | 1.87E−09 |

TABLE 4-continued

The detailed list of prediction pathways and diseases of high-dose Virofree from multi-databases. Virofree 500 μg/nl (high dose)

| Pathway description | p-value |
|---|---|
| BMP signaling pathway | 2.03E−09 |
| Cardiac septum development | 2.75E−09 |
| Response to hypoxia | 3.06E−09 |
| Cellular response to steroid hormone stimulus | 3.8E−09 |
| Cell junction assembly | 4.16E−09 |

Additionally, PCA analysis was performed to compare the transcriptomic response to low and high doses of Virofree (FIG. 1E-F). PC1 can mainly describe the transcriptomic profile of high-dose treatment, whereas PC2 can describe the transcriptomic profile of low-dose treatment (FIG. 1E). The gene loading scores on each principal component (PC) can demonstrate the distribution of that gene in the PC, or in other words, the expression pattern of that gene in the sample. A positive loading score indicates the gene expression and a PC are positively correlated. In the case of PC1, since the expression profile of high-dose Virofree treatment is enriched in the positive PC1, genes with positive loading scores in PC1 tend to be up-regulated, similar to PC2 and the low dose of Virofree treatment response profile. A negative loading score indicates a negative correlation, therefore, genes with negative loading scores are probably downregulated. A higher magnitude of (either positive or negative) loading scores demonstrates a stronger effect on that PC. The distribution of the loading scores of the two PCs is indicated in FIG. 1F. In general, genes related to iron homeostasis including FTH1 and SLC7A11 encoding xCT were up-regulated in both doses of Virofree, indicating a protective effect against ferroptosis. Interestingly, IL6 was also downregulated by both doses of Virofree, compared with the control, indicating promising effects of Virofree in blocking the IL-6 signaling pathway to inhibit the cytokine storm. Additionally, fibronectin (FN1) expression level is likely to decrease with high-dose Virofree treatment, suggesting the inhibitory effect on fibrosis. The alteration in the expression of these genes was validated in later experiments.

3. Virofree Significantly Up-Regulates Targeter miRNAs to Affect SARS-CoV-2

Since upregulating the expression of let-7a-5p and miR-148b-5p was likely beneficial in treating COVID-19 [33], the effects of Virofree on the expression of these miRNAs were studied. Additionally, the top 100 genes with positive loading scores in the PC1 PCA analysis also show significant enrichment in a gene set containing miRTarBase let-7a-5p targets (p-value=0.002; the analysis was performed by CPDB).

Figure 10:
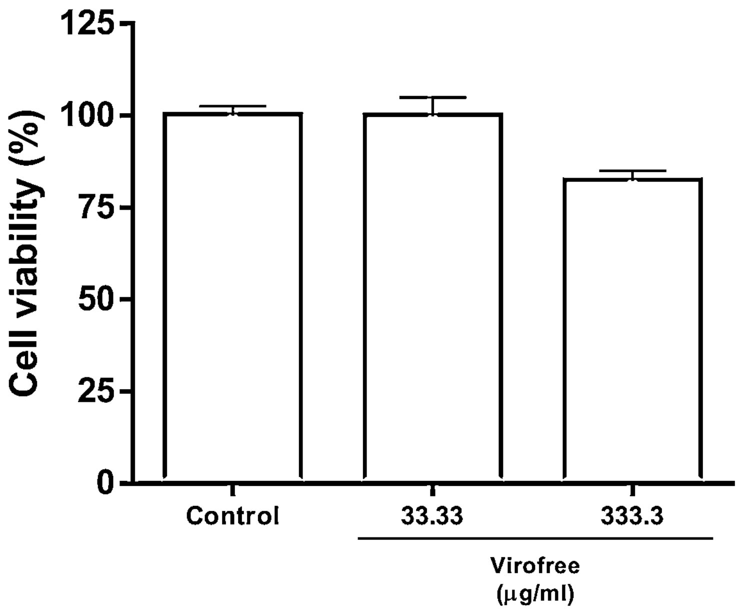
FIG. 10 shows the Cytotoxicity of Virofree treatments; After 24 h of Virofree treatments, BEAS2B cells were collected and measured the survival rate by SRB assay (n=3). All data are presented as means±SD.
Figure 11:
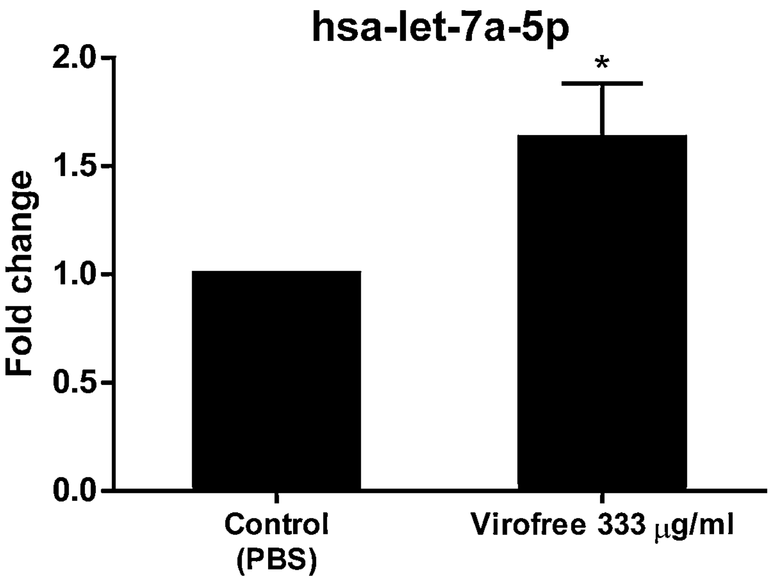
FIG. 11 shows the Virofree can potentially reduce viral replication by inducing let-7a-5p; let-7a-5p expression levels were measured by qRT-PCR after 24 h treated with 333 μg/ml of Virofree (n=3). All data are presented as means±SD. Statistical analysis was carried out with a t-test. *: significantly different from the corresponding control respectively with p<0.05.

First, the highest safe dosage of Virofree was determined by treating BEAS-2B cells with different concentrations for 24 h in 96-well plates and evaluating cell viability using the SRB assay. Treated cells maintained a viability rate of more than 80% (FIG. 10). The qRT-PCR results showed that a low dose of Virofree (33.3 μg/ml) could significantly increase miR-148b-5p expression by 3.71-fold (FIG. 2A), whereas the high dose of Virofree (333 μg/ml) could increase let-7a-5p expression by 1.63 folds (FIG. 11). These results suggested that Virofree could upregulate the expression of targeted miRNAs in a dose-independent manner.

4. Virofree Effectively Suppresses the Cleavage of SARS-CoV-2 $M^{pro}$

Proteolytic cleavage of SARS-CoV-2 polyproteins pp1a and pp1ab by $M^{pro}$ residing on nsp5 releases nsp5-16 and the carboxy (C) terminus of nsp4, whose functions are required for viral replication [34]. SARS-CoV-2 $M^{pro}$ is a promising target for therapeutic intervention against COVID-19. Therefore, the peptide containing the cleavage site between nsp4 and nsp5 was labeled with a fluorophore (Abz) and its quencher (Dnp) at N-terminus and C-terminus respectively for measuring the protease activity of SARS-CoV-2 $M^{pro}$. The repression of recombinant SARS-CoV-2 $M^{pro}$ activity was examined by Virofree as the inhibitor in protease activity assay using a fluorogenic probe. The result showed that Virofree could inhibit $M^{pro}$ activity with $IC_{50}$ at 19.71±43.94 μg/ml (FIG. 2B), indicating that the drug could suppress SARS-CoV-2 $M^{pro}$ activity.

5. Virofree can Inhibit the Cytokine Storm in Macrophages

To quantify the released amount of TNF-α, one of the most abundantly detected cytokines in the plasma acute-phase COVID-19 patients [35], cell medium was collected at 6 or 24 h Virofree post-treatment to perform ELISA. LPS stimulator treatment alone was considered as the control. Virofree showed its potential in TNF-α suppression in the presence of LPS. The higher dose of Virofree demonstrated a better effect with notable inhibition at both time points, whereas the lower dose could only slightly decrease TNF-α secretion levels at time-point 6 h (FIG. 2C). These data suggest that Virofree could partially reduce cytokine storm by inhibiting TNF-α release.

Figure 12:
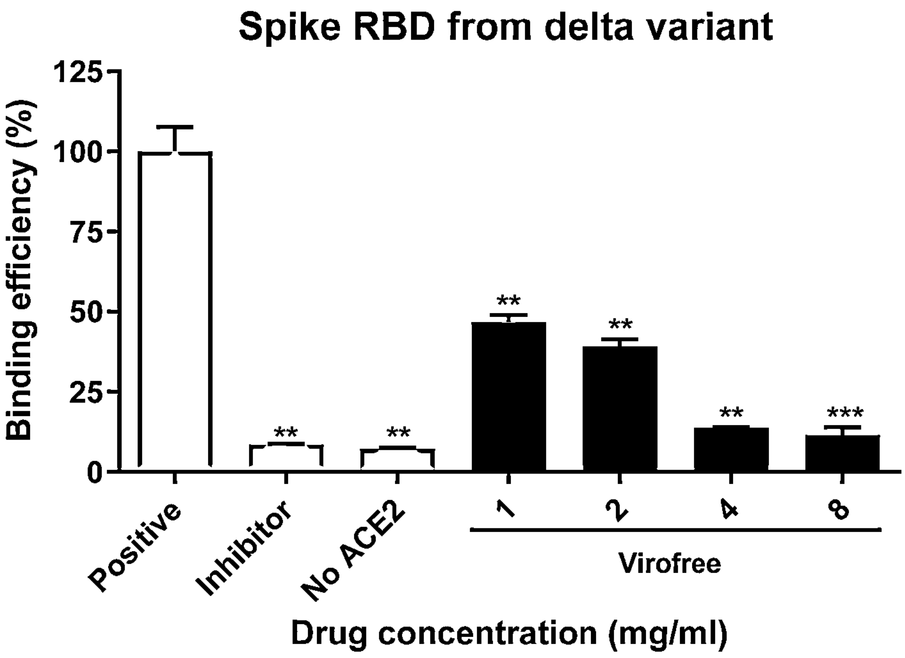
FIG. 12 shows the inhibitory activity of Virofree against the Delta RBD spike protein binding to ACE2; RBD spike protein derived from variant Delta was used for ELISA-based spike protein and hACE2 binding assays; a positive condition represents the full binding activity of trimeric spike protein on hACE2; the inhibitor used was the wild-type spike RBD antibody (10 μg/mL). Data represent Mean±SEM (n=4). A  or * indicates a significant difference to the corresponding control sample with p<0.01 or 0.001, respectively when compared to the binding efficiency of the positive group.

6. Virofree Interrupts the Binding of Trimeric SARS-CoV-2 Spike Protein Wild-Type (Wuhan Strain) or Variants (α,β, γ, δ, and o) to Biotinylated Human ACE2 Recombinant Protein To investigate whether Virofree has a direct inhibitory effect on the binding between SARS-CoV-2 S protein and ACE2, an in vitro biochemical binding ELISA assay was conducted using recombinant SARS-CoV-2 S protein and ACE2 and the inhibitory effect of Virofree at doses of 1, 2, 4, and 8 mg/ml was examined. Virofree suppressed the binding efficiency of all five trimeric spike protein strains to ACE2 by approximately 25%-50% (FIG. 3A-F). Among them, Virofree appeared to be more effective against the spike proteins of the Delta and Omicron strains than the others (FIGS. 3E and F). Virofree inhibitory activity against RBD of the Delta variant spike protein was also observed with similar potency against the trimeric form (FIG. 12). Wild-type spike RBD antibody (10 μg/ml) appeared to be ineffective against the Omicron variant spike protein. These findings suggested that Virofree could directly disrupt the interaction of ACE2 with SARS-CoV-2 S proteins from multiple varitents including Omicron.

7. Suppression of the Binding of SARS-CoV-2 Spike Protein to ACE2 Receptor and its Formation of Syncytium of Virofree Via Cell-Based Assays Viral proteins expressed on infected cell membranes can interact with receptors on neighboring naïve cells, resulting in cell-cell fusion and syncytia formation [36]. Receptor-dependent syncytia formation is triggered by SARS-CoV-2 spike (S) protein in the cell membrane [37-39]. Therefore, to further elucidate the anti-SARS-CoV-2 activity of Virofree, the effects of Virofree were measured on both binding efficiency and fusion efficiency between BHK-21 cells, in which wild-type or Delta-variant SARS-CoV-2 spike proteins were co-expressed with EGFP, and Calu-3 cells with endogenous hACE2 receptor expression. The binding of the BHK-21 cells to Calu-3 cells indicated the interaction of the SARS-CoV-2 S protein with the ACE2 receptor. Furthermore, syncytium formation was caused by membrane fusion between BHK-21 and Calu-3 cells.

Figure 4:
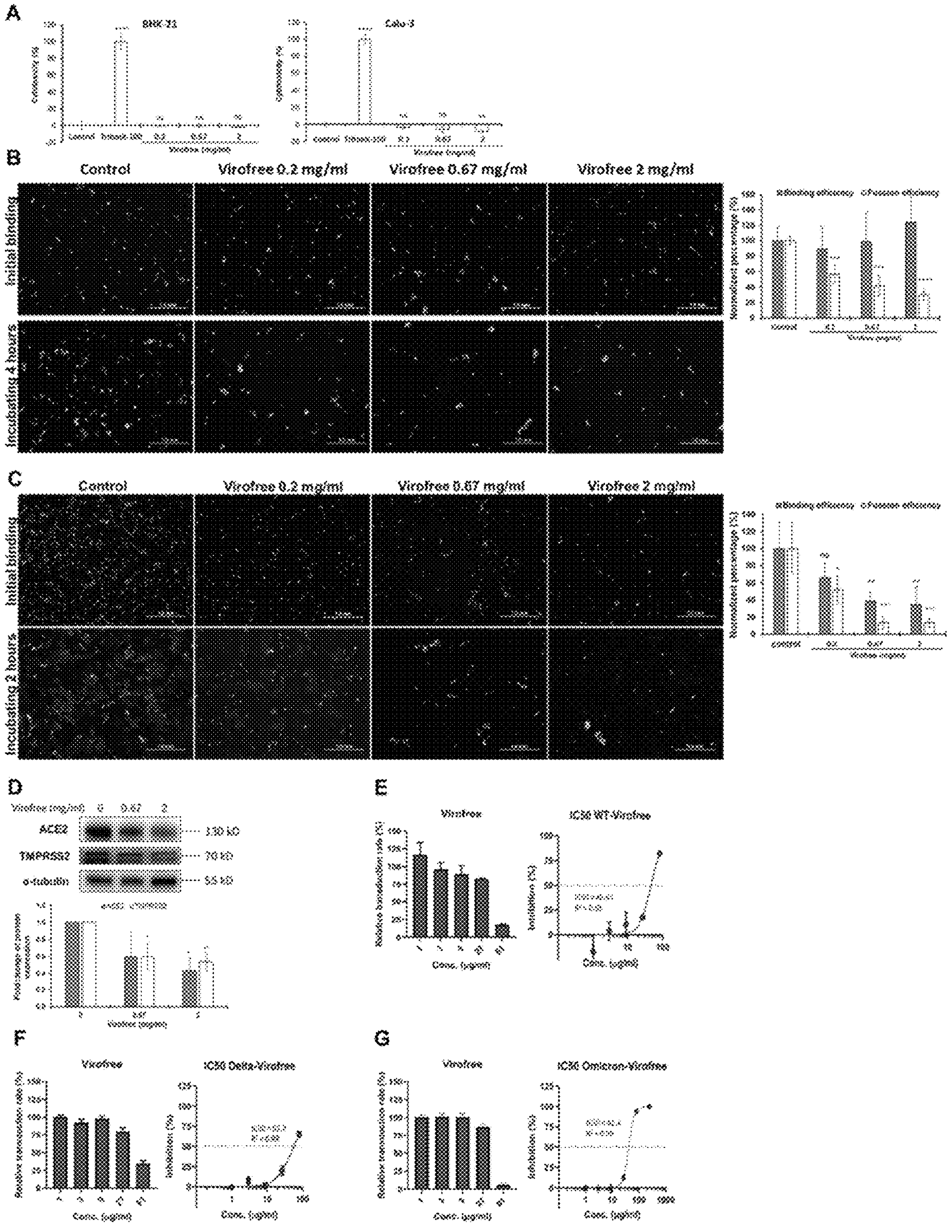
FIG. 4 shows the Virofree can interfere with SARS-CoV-2-spike-mediated binding and syncytium formation in cell-based assays; (A) the cytotoxicity of Virofree was validated by LDH cytotoxicity assay. BHK-21 and Calu-3 cells were treated with indicated amounts of Virofree and the cellular cytotoxicity of Virofree was determined by LDH assay; the control group represented no Virofree-treated group, using as a negative control; the treatment with Triton-100 was serving as a positive control. The data were presented as the mean±SD; error bars indicated SD. ns indicated non-significant compared to the control group. p<0.01, **p<0.0001. (B-C) EGFP and wild-type (B) or Delta (C) Spike Co-expressed BHK21 cells were added into Calu-3 cells and incubated at 4° C. for 1 h for Spike-ACE2 binding; after 4 h (wild-type) or 2 h (Delta) of incubating, the big fluorescence multinucleate cells were formed in the control group, indicating spike-mediated syncytium formation; the histogram depicts the binding and fusion efficiency in each group (n=3); (D) Calu-3 cells were treated with 0, 0.67, 2 mg/ml of Virofree for 5 h (n=3). (E-G) Virofree can block the infection of pseudovirus expressing SARS-CoV-2 spike protein in ACE2-expressing HEK293T cells in a cell-based neutralizing assay; the inhibitory effect with ICso of Virofree on the entry of wild-type (E), Delta (F), or Omicron (G) SARS-CoV-2 in pseudovirus neutralizing assay (n=3). All data are presented as means±SD. *p<0.05, p<0.01, *p<0.001, ****p<0.0001.

To confirm the cytotoxicity of Virofree to BHK-21 and Calu-3 cells, both cells were treated with various concentrations from 0.2 to 2.0 mg/ml of Virofree. The treatment of Triton-100 was serviced as a positive control, and the control group was represented a non-treatment group. LDH assay clearly showed that Virofree treatment caused no significant amount of cell death, compared to the control group, indicating no cytotoxicity of Virofree to either BHK-21 cells or Calu-3 cells (FIG. 4A). In FIG. 4B, compared to the control group, there was no significant difference in binding efficiency of BHK-21 cells with Calu-3 cells among various Virofree treatment groups. After 4 h of incubation, multinucleated cells with expanded green fluorescence signals were formed in the control group, indicating spike-mediated syncytium formation.

Furthermore, the wild-type spike-mediated syncytium formation was significantly reduced dose-dependently by Virofree treatment. While the SARS-CoV-2 spike Delta variant was expressed in BHK-21 cells, in contrast, Virofree treatment not only caused decreased binding of BHK-21 cells to Calu-3 cells but also significantly inhibited syncytium formation (FIG. 4C). Western blot assay revealed that Virofree treatment dose-dependent reduced ACE2 and TMPRSS2 expression (FIG. 4D). The fusion-blocking effect of Virofree was further demonstrated through a cell-based pseudovirus neutralizing assay. The result showed that Virofree could inhibit the entry of pseudoviruses with either wild-type (FIG. 4E), Delta (FIG. 4F), or Omicron (FIG. 4G) of SARS-CoV-2 spike with the $IC_{50}$ at 46.50, 57.71, and 42.40 μg/ml, respectively.

Figure 13:
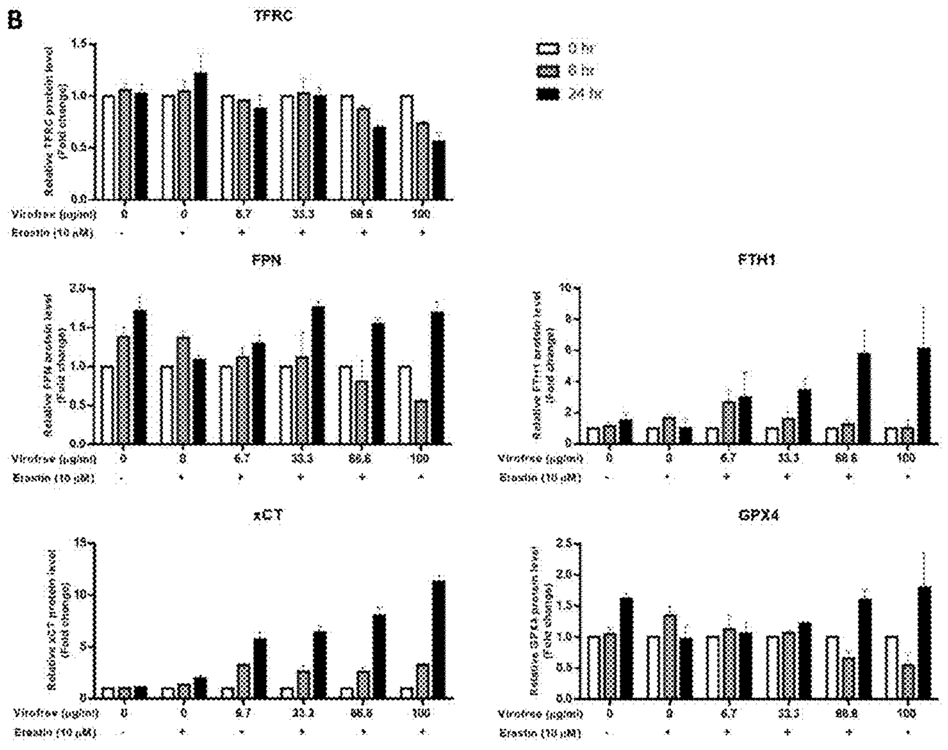
FIG. 13 shows the quantification of Virofree reducing labile iron pool and protecting the cells from ferroptosis in THP-1-derived macrophages; (A) THP-1-derived macrophages received treatments of different concentrations of Virofree for 6, or 24 h, respectively; GAPDH was used as an internal control (n=3); (B) THP-1-derived macrophages received treatments of different concentrations of Virofree in the presence of erastin (10 μM) for 6, or 24 h, respectively. GAPDH was used as an internal control (n=3). All data are presented as means±SD. A *, , *, or **** indicates a significant difference to the corresponding control sample with p<0.05, 0.01, 0.001, or 0.0001, respectively.
Figure 14:
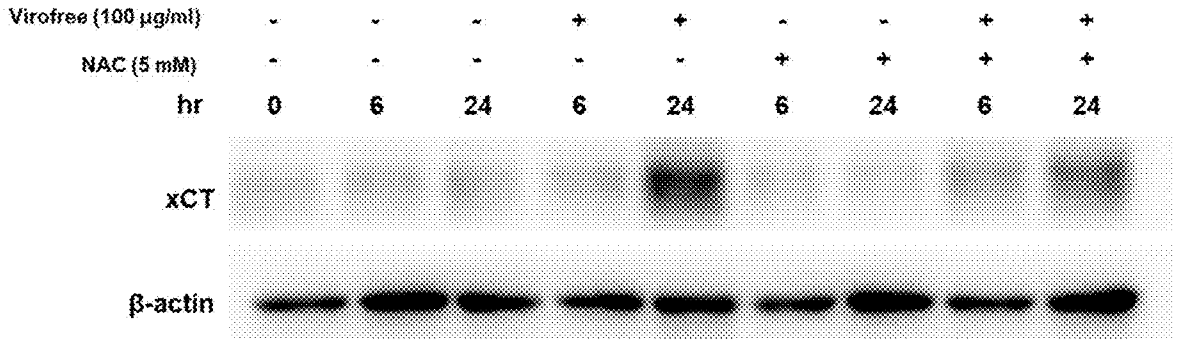
FIG. 14 shows the reduction of ROS levels mediated by NAC decreased the expression levels of xCT mediated by Virofree; THP-1-derived macrophages were pretreated with 5 mM NAC for 1 h and then treated with 100 μg/ml of Virofree for 6, or 24 h, respectively; whole-cell lysates were prepared and subjected to western blot analysis. β-actin was used as an internal control.

8. Virofree Prevents Macrophages from Oxidative-Mediated Toxicity and Ferroptosis To investigate the expression of proteins involved in iron homeostasis in Virofree-treated THP-1-derived macrophages, cells were collected after THP-1 macrophages were incubated with different Virofree concentrations, followed by western blotting to detect the protein expression levels. The expression of FTH1 and xCT increased dose-dependently in THP-1 macrophages after being treated with Virofree (FIG. 5A)(FIG. 13). The results indicate that Virofree might have the potential to enhance the prevention of ferroptosis in macrophages by increasing the expression levels of xCT and FTH1. The protective effects and mechanisms of Virofree against ferroptosis merit further investigation. N-acetyl cysteine (NAC) pretreatment could significantly decrease xCT expression, indicating that elevated ROS levels could induce xCT expression to protect cells (FIG. 14). To further determine if Virofree could serve as a ferroptosis inhibitor, erastin was used to observe whether Virofree could rescue erastin-induced ferroptosis in cells. Based on western blot results, Virofree can rescue the downregulated expression levels of ferroportin (FPN) and GPX4, an antioxidant enzyme (FIG. 5B), indicating that Virofree could prevent erastin-induced ferroptosis in THP-1 macrophages.

9. Virofree could Inhibit the Expression of TGF-β1-Induced α-SMA and ECM Proteins.

Figure 6:
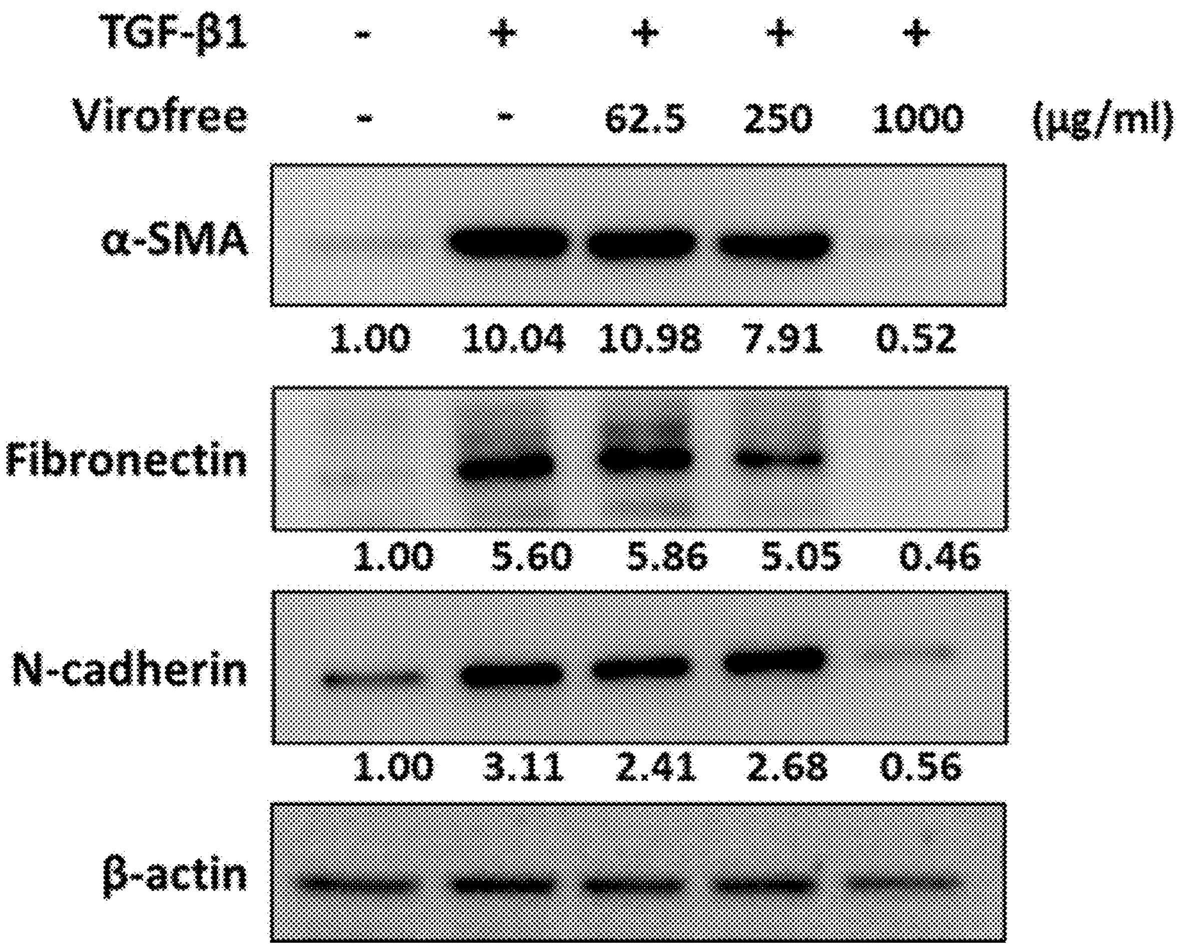
FIG. 6 shows the Virofree inhibits TGF-β1-induced α-SMA and ECM protein expression; LL29 cells were co-treated with 2.5 ng/ml TGF-β1 and Virofree at different concentrations for 48 h. Quantification showed a suppressive effect of Virofree on the expression of α-SMA, fibronectin, and N-cadherin expression via Western blot analysis (n=3). All data are presented as means±SD. *p<0.05, p<0.01, *p<0.001.
Figure 9:
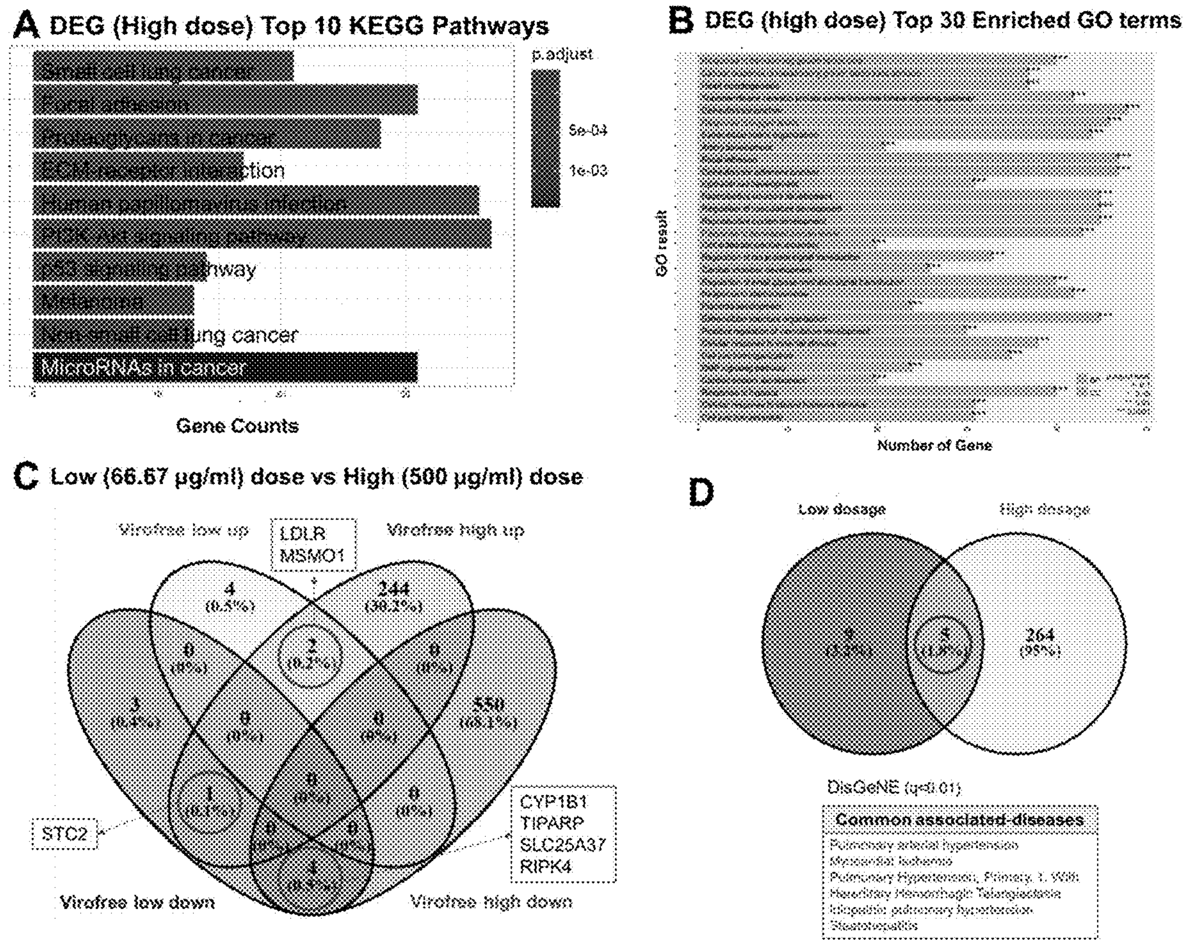
FIG. 9 shows the different dosages of Virofree connected similar mechanisms through bioinformatics analysis; the highly potential disease mechanisms of high dose (500 μg/ml) of Virofree from big data analysis; (A) the bar plot showed the top 10 pathways from KEGG enrichment analysis on the DEGs list; the intensity of color denotes the p-value, and the length of the bar indicates the overlapped genes ratio (gene counts) between the DEGs and pathways; (B) the bar plot demonstrated the top 30 pathways of high Virofree from Gene Ontology (GO); the color means the classification of the gene, such as Biological Process (BP) and Cellular Component (CC); the length of the bar indicates the overlapped genes number between the DEGs and GO terms; the analysis results were listed in (Table 4); (C-D) The effects on genes expression levels and associated diseases of low dose (66.67 μg/ml) of Virofree were compared with the effects of high dose (500 μg/ml) of Virofree; (C) Venn diagram intersected the common DEGs among 4 sets and 2 genes (LDLR and MSMO1) were up-regulated at both doses as well as 4 genes (CYP1B1, TIPARP, SLC25A37, and RIPK4) were downregulated at both. However, expression levels of STC2 were changed between low and high dosage; the threshold is 1.5 log 2 fold change and the q value<0.01. (D) We intersected the disease results between two concentrations and showed 5 common diseases in both treatments; especially, pulmonary arterial hypertension was one of the elements that Virofree was the candidate drug to treat ARDS.

COVID-19 infection can lead to ARDS, and may potentially cause pulmonary fibrosis with lifelong sequelae [40]. TGF-β1 plays an important role in the pathogenesis of fibrotic lung disease by promoting the differentiation of fibroblast cells to myofibroblast cells [41], and stimulating the synthesis of ECM components, eventually leading to abnormal fibrosis [42]. To confirm the inhibitory effect of Virofree on fibrosis, LL29 cells were treated with TGF-β1 and Virofree for 48 h. The results indicated that Virofree can significantly inhibit TGF-β1-induced α-SMA protein expression dose-dependently. Moreover, N-cadherin expression level was reduced dramatically by the treatment with Virofree 1,000 μg/ml. In addition, we observed a reduction in TGF-β1-induced fibronectin protein expression level after LL29 cells were treated with Virofree 1,000 μg/ml (FIG. 6, FIG. 9). These data indicate Virofree had an inhibitory effect on TGF induced fibrosis.

Figure 7:
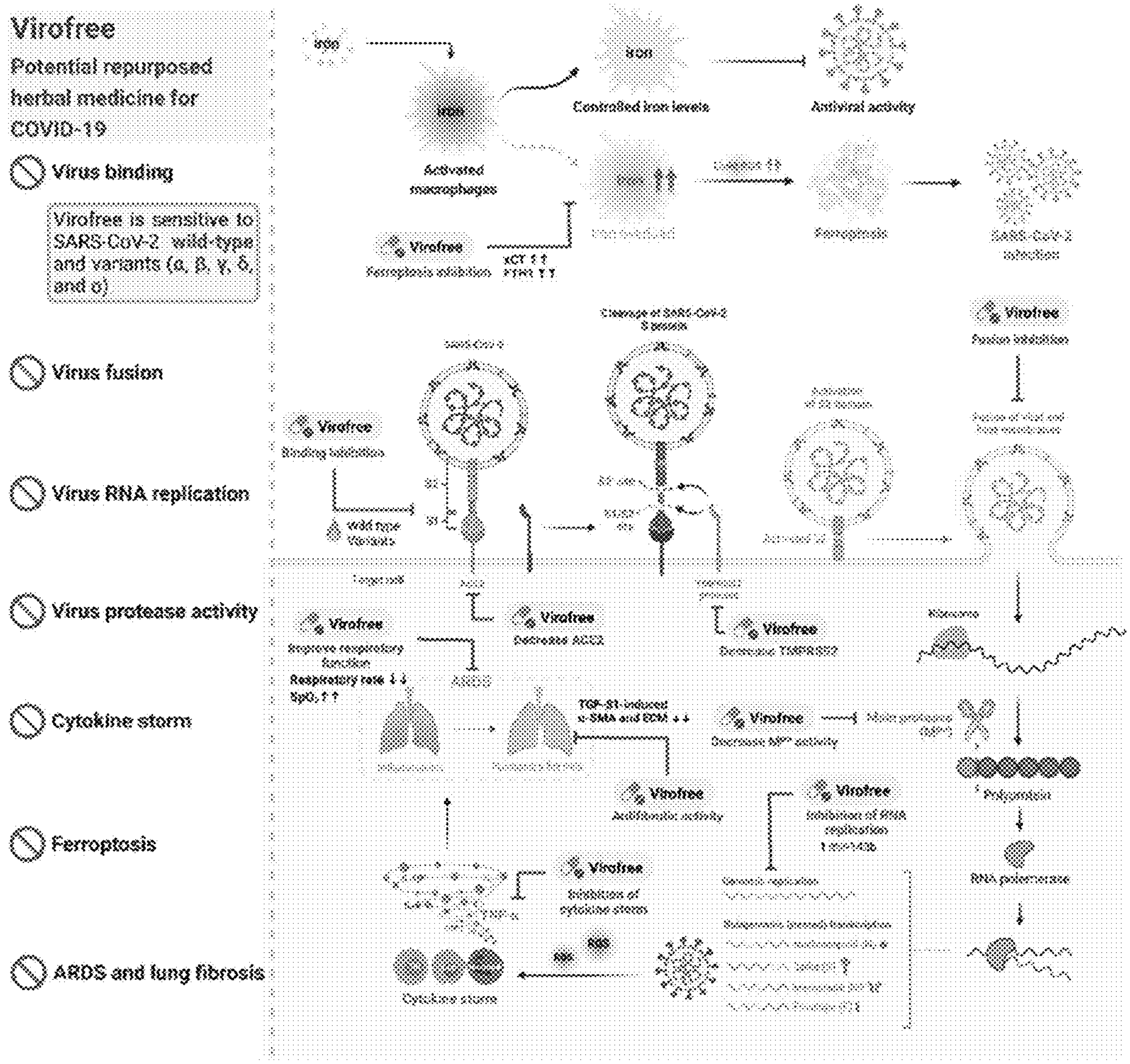
FIG. 7 shows the Virofree is a candidate therapeutic treatment for COVID-19; the invasion of the virus into host cells through the replication process may result in cytokine storm and multi-organ failure. Iron uptaking is one of the symptoms observed in COVID-19 patients, which may lead to ferroptosis promoting viral infection. In our study, Virofree could serve as a ferroptosis inhibitor and antiviral agent by suppressing viral entry and fusion of wild-type and multiple variants of SARS-COV-2 spike via reducing ACE2 and TMPRSS2 protein expression, inhibiting viral protease activity, increasing mir-148b, targeting cytokine storm, as well as downregulating fibrosis proteins in vitro. The fainted patterns illustrate for the reduction or inhibition (created with BioRender.com).

In summary, Virofree exhibited multiple functions for targeting SARS-CoV-2. Virofree (1) blocked virus entry by interrupting protein binding between the different subtypes of spike and ACE2, as well as reducing ACE2 and TMPRSS2 protein expression, (2) decreased viral replication by increasing miR-148b level and inhibiting Mpro activity, (3) contributed to cytokine storm reduction by repressing LPS-induced TNF-α production, (4) prevented ferroptosis of THP-1 macrophages, and (5) reduced TGF-β1-induced fibrosis in vitro. Our study reveals that Virofree is a promising herbal medicine for further COVID-19 preclinical and clinical studies on the emergence of the Delta and Omicron variants and their transmission (FIG. 7).

Discussion

As of Sep. 30, 2021, the FDA has announced more than 640 drug development programs in the planning stages, 470 more reviewed trials, 11 treatments authorized emergency use, and only 1 approved treatment. Remdesivir is the first and only approved drug that targets antiviral replication. Several larger cohorts captured observational data on Remdesivir outcomes, reporting a lower risk of death and clinical improvement in the early illness stage [43, 44] but not overall mortality benefit for all hospitalized patients and no significant different response in patients with severe COVID-19 [45]. Other therapeutic strategies were immunomodulators (Baricitinib (JAK inhibitor), Tocilizumab (IL-6 receptor blocker)), and spike protein monoclonal antibodies (such as Casirivimab/Imdevimab, Bamlanivimab/Etesevimab) that showed limitations in the effectiveness of treatment for some patients [46]. Not to mention ongoing clinical trials, lopinavir-ritonavir, intravenous ribavirin, umifenovir, corticosteroids, or interferon-alpha-2b did not report the consistent clinical benefit [47]. Recently, Omicron has emerged in a COVID-19-weary world, which has higher transmissibility, and viral binding affinity. Importantly, the effects of most of the remaining Omicron mutations are unknown, leading to a high level of uncertainty about the effects of the entire combination of deletions and mutations on viral behavior and susceptibility to natural and vaccine-mediated immunity. The increase in reinfection cases is consistent with the immune-escape mutations present in Omicron [48]. Until now, only Nirmatrelvir is effective against Omicron in vitro [49]. According to previous publications, the pathological process of SARS-CoV-2 infection starts with the binding of viral spike protein and the human ACE2 receptor, eventually entering cells, replicating, forming new The protease is then cleaved into two small polypeptides fragments (pp1a and pp1b) for viral replication and transcription [50, 51]. Proteolysis then packages the components for a new virion by the coronavirus main protease (Mpro) and releases the functional viral polypeptide [51, 52]. These latter factors trigger the cytokine level and dysregulate iron concentration, leading to ferroptosis and fetal ARDS syndrome. In general, there was more than one mechanism to control the pathogenesis of SARS-CoV-2, the current treatment targeted a single biological function that would ignore other signals of the virus' ferocity. Therefore, it is necessary to discover a new drug with multiple functions that completely interrupts SARS-CoV-2 infection.

Big data analysis provides a systematic and comprehensive approach to drug development by linking drug response profiles with disease signature and mechanism of action. Large-scale screening of compound reference profiles against the COVID-19 signature via GSEA suggested that Virofree, a safe and healthy herbal medicine, was one of the potential candidates (FIG. 1A). The enrichment analysis revealed that Virofree could aim at multiple targets for COVID-19 treatment. The top-ranking KEGG and GO enriched pathways included iron-ion homeostasis, iron-ion binding, and ferroptosis (FIG. 1B-D). COVID-19 patients had abnormally lower serum iron levels (<7.8 μmol/L) and hyperferritinemia in several prevalence studies [53, 54], in which iron dysregulation and overload stimulated the generation of ROS to damage organs leads to inflammatory activation. The HIF-1 (hypoxia-inducible factor-1α) signaling pathway plays an important role in virus infection and proinflammatory responses [55, 56], was significantly enriched in gene expression profiles of Virofree treatment (FIG. 1B), suggesting effects of the drug on this pathway to suppress IL-6 production, which is consistent with PCA loading scores (FIG. 1F), and eventually inhibit the cytokine storm. GO enrichment that indicated Virofree can mediate clathrin-coated pit [57] and virus receptor activity, which are related to virus-human entrance interaction In contrast, the disease association via DO shows many COVID-19 symptoms or diseases in the upper range to Virofree treatment, including iron metabolism disorders, pulmonary arterial hypertension, idiopathic pulmonary hypertension, airway obstruction, and the common cold. In general, Virofree can regulate the comprehensive pathological mechanisms of SARS-CoV-2 through different mechanisms and our results agree with previous studies and clinical evidence. Recently, different SARS-CoV-2 variants were explored that made the treatment more difficult and complex. Virofree response profile and these variants signatures can be analyzed further the to determine the suitable treatment regimen.

Experimental validation proved that Virofree increased the expressions of let-7a-5p and miR-148b-5p in BEAS-2B cell lines (normal bronchial epithelial cells). The let-7 family attenuates the diversity of viral infection, for example, the virulence of influenza viruses interruption, which associates pneumonia and ARDS symptoms [33]. Sardar et al. [59] mentioned that let-7a targeted nonstructural proteins of SARS-CoV-2 and Chauhan et al. [60] reported that other family members can regulate TMPRSS2. As the immunomodulator, let-7a could bind to the TLR4 mRNA strand to block downstream MyD88 and NF-κB signaling including IL-6, which drives innate immunity and proinflammatory response (TNF-α activation) [61]. Meanwhile, miR-148a plays another modulator in the proinflammation, a target miRNA of TLR3, which also regulates the IKK/NF-κB pathway, MyD88, and cytokines (IFN-Δ, IFN-β, IL-6, IL-8) [62]. Some studies predict that miR-148a is a high potential candidate for targeting the SARS-CoV-2 genome through bioinformatics [63, 64]. Although the regulation among miR-148b-5p, let-7a-5p, and cytokine production was not elaborate, Virofree stimulated these two miRNAs' expression levels (FIG. 2A and FIG. 11) and reduced TNF-α (FIG. 2C). In the above-mentioned evidence, Virofree demonstrated the multiple functions (miRNAs and cytokines) to suppress the SARS-CoV-2 pathological mechanism.

Furthermore, Virofree showed two additional functional properties including inhibition of $M^{pro}$ to stop virus replication and interruption of SARS-COV-2 S protein binding to ACE2 to block viral entry. The SARS-CoV-2 replica gene encodes two overlapping polyproteins, pp1a and pp1ab, that are required for viral replication and transcription. Functional polypeptides are released from polyproteins through the protein hydrolysis processes, primarily by $M^{pro}$ (also known as 3C-like protease). $M^{pro}$ digests polyproteins at 11 conserved sites. The functional importance of $M^{pro}$ in the viral life cycle and the absence of closely related homologs in humans [65-67], places $M^{pro}$ identified as a tempting target for antiviral drug design. The enzymatic assay showed that Virofree could inhibit $M^{pro}$ activity at $IC_{50}$ of 19.71±43.94 μg/ml (FIG. 2B).

Figure 3:
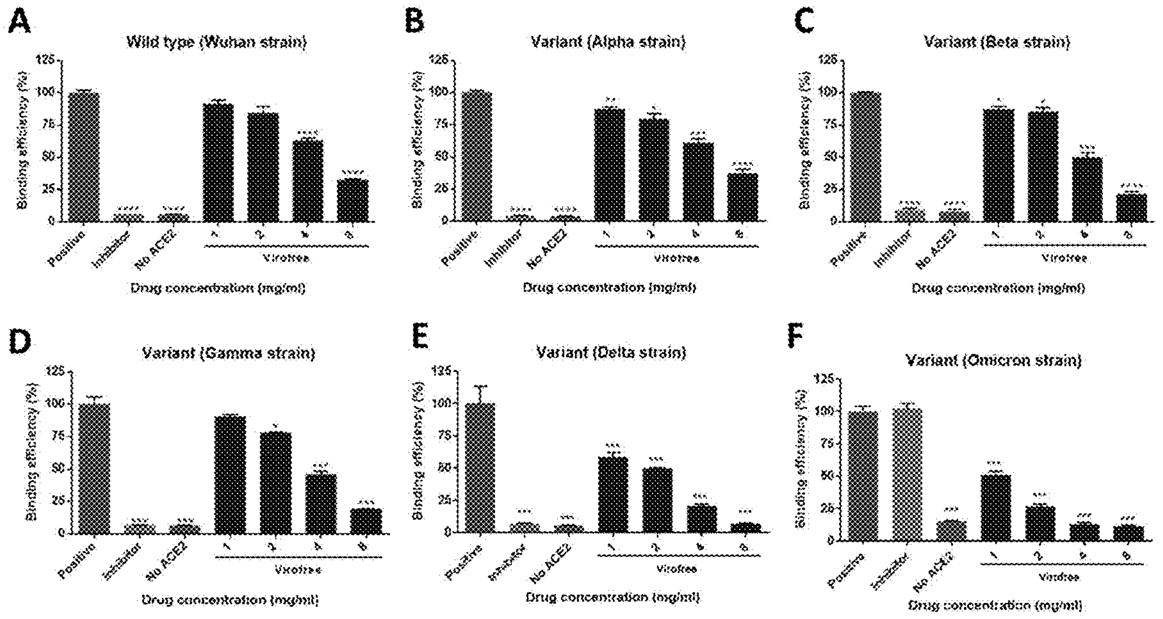
FIG. 3 shows the variant specificity of Virofree against the trimeric spike protein binding to ACE2; (A-E) Trimeric spike proteins derived from (A) wild-type/Wuhan strain, (B) variant Alpha, (C) variant Beta, (D) variant Gamma, (E) variant Delta, and (F) variant Omicron was used for ELISA-based spike protein and hACE2 binding assays; a positive condition represents the full binding activity of trimeric spike protein on hACE2; the inhibitor used was the wild-type spike RBD antibody (10 μg/ml). Data represent Mean±SEM (n=4). A *, , or * indicates a significant difference to the corresponding control sample with p<0.05, 0.01, or 0.001, respectively when compared to the binding efficiency of the positive group, correspondingly.

The ELISA-based trimeric spike-ACE2 binding assay demonstrated that Virofree can block binding between ACE2 and several spike proteins, including wild-type, α, β, γ, δ, and o variants (FIG. 3). Additionally, the result also suggested that the inhibitory effect of Virofree against the spike protein might be related to the RBD of the spike protein. Among these variant spike proteins, the Delta and Omicron variants showed the most sensitive inhibition by Virofree (FIG. 3E, F).

The inhibitory activity of the wild-type spike RBD antibody against the Omicron variant spike protein was not observed. This observation is consistent with the recent report showing that COVID-vaccine protection is weaker against Omicron [68]. As a result, Virofree appears to show a broader spectrum against spike proteins derived from various variants compared with the target-specific RBD antibody. The results of the cell-cell fusion assay showed that the binding of Delta spike and ACE2 could be inhibited by Virofree treatment (FIG. 4C), which is in line with the results of the ELISA-based trimeric spike-ACE2 binding assay (FIG. 3E).

Figure 15:
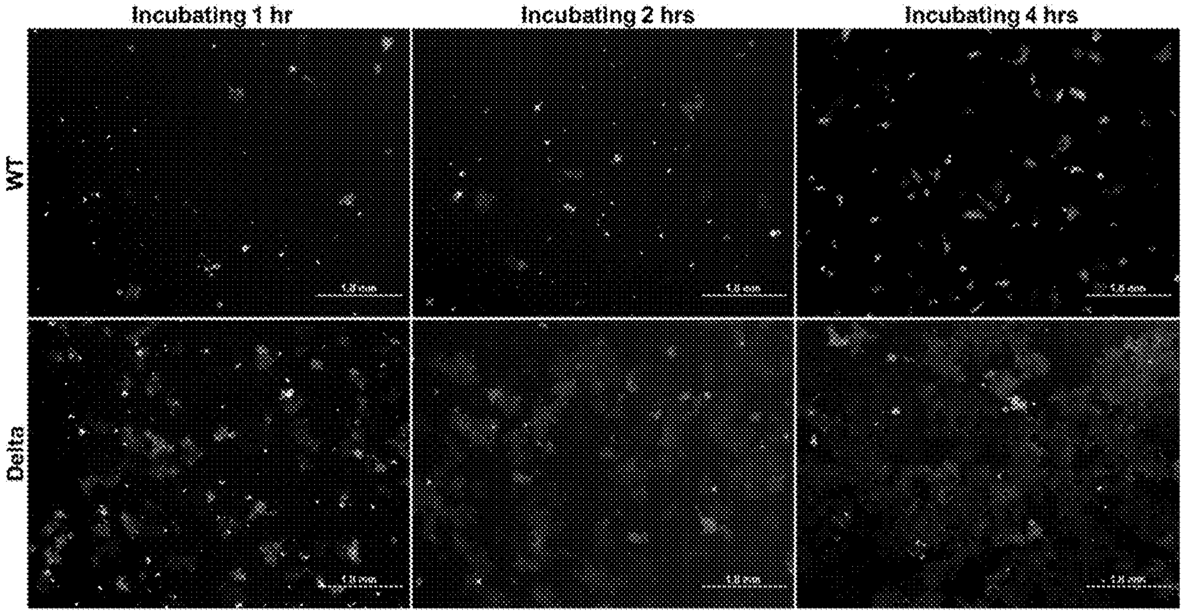
FIG. 15 shows the time-course assay for syncytium formation of both wild-type and Delta spike-expressed BHK21 to ACE2-expressed Calu-3 cells; EGFP and wild-type (upper panel) or Delta (lower panel) Spike Co-expressed BHK21 cells were added into Calu-3 cells and incubated at 37° C. for 1, 2, or 4 h; the big fluorescence multinucleate cells were formed in the control group, indicating spike-mediated syncytium formation

Furthermore, SARS-CoV-2 spike-mediated syncytium formation could mean that virus-induced cell fusion facilitates viral genomes delivery to neighboring cells [69]. While examining the histopathologic lung sections from deceased COVID-19 patients, the prevailing existence of syncytia cells containing 2-20 nuclei was observed, indicating the correlation between syncytia formation and severe pathogenesis. Based on these observations, using spike-mediated cell fusion to validate drugs against SARS-CoV-2 infection could be a potent strategy [70]. The time-course experiments were conducted in both wild-type and Delta spike proteins (FIG. 15). Compared with the wild-type, the Delta strain showed higher binding ability at the initial binding step and faster fusion kinetics at the following time points. The Delta variant reached almost complete fusion within 2 hours; in contrast, the percentage of cell fusion in the wild-type remained relatively low. Therefore, we have illustrated the fusion results of the Delta variants at the time point of two hours, instead of four hours (FIG. 4B).

The results of the cell-cell fusion assay clarified the suppression of spike-mediated cell-cell fusion and pseudovirus infection by Virofree treatment (FIGS. 4B, 4C and 4E), implying that Virofree may not only interrupt the binding of variant spikes and ACE2 but also affect host protease-involved SARS-CoV-2 membrane fusion. In both ELISA and cell-cell fusion assay, Delta variants displayed higher sensitivity to Virofree treatment, compared with wild-type S protein. Because the spike-mediated syncytium formation of the Delta strain was stronger than that of other SARS-CoV-2 variants [71], Virofree which can inhibit the binding of Delta spike and ACE2 sensitively would become a potent drug against Delta variant infection. Additionally, western blot assay revealed that Virofree treatment could reduce TMPRSS2 expression dose-dependently (FIG. 4D), suggesting that Virofree inhibition of SARS-CoV-2 infection could be due to decreased expression of TMPRSS2, which can cleave the SARS-CoV-2 S protein to trigger membrane fusion of SARS-CoV-2 and host cells to facilitate virus entry [72]. Taken together, these findings indicated that Virofree could inhibit viral binding and entry through two different mechanisms: the inhibition of ACE2 and TMPRSS2 expression, and the direct interruption of SARS-CoV-2 S protein binding to ACE2.

Furthermore, recent studies also revealed the pathological role of spike proteins not only in promoting pulmonary vascular remodeling and vascular endothelial cell dysfunction but also in causing pulmonary arterial hypertension [73]. ACE2 acts as a receptor in response to spike protein stimulation [74]. Therefore, inhibition of spike protein binding to ACE2 by Virofree may also contribute to lung protection in addition to preventing viral infection.

Figure 2:
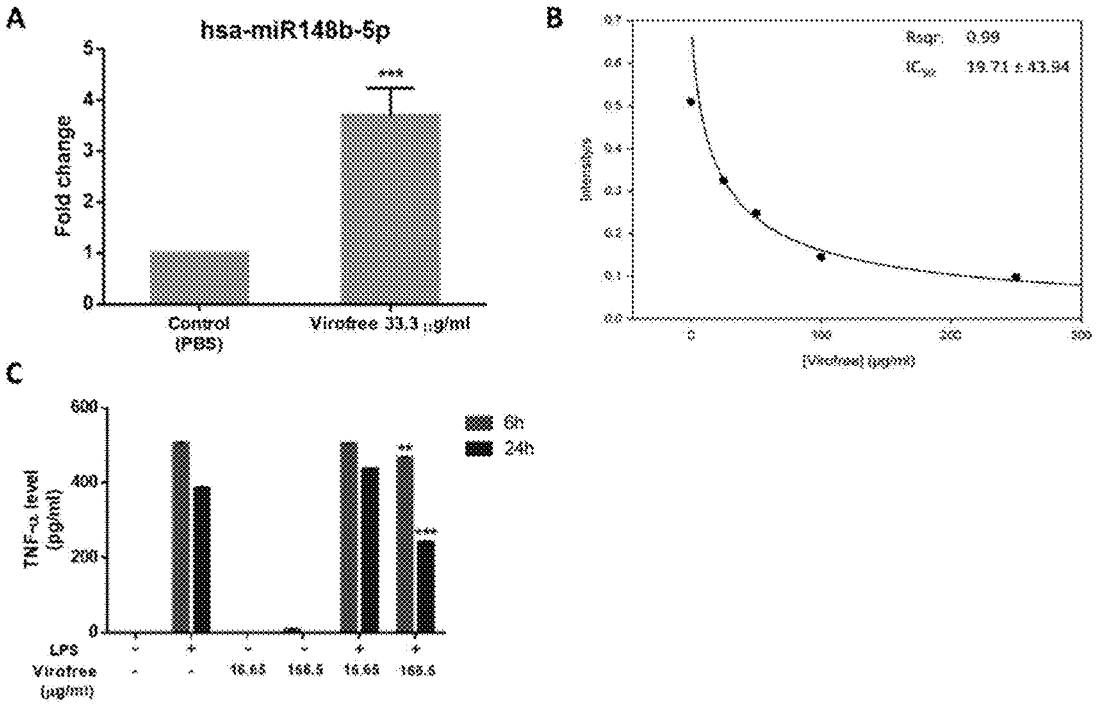
FIG. 2 shows the herbal composition of the invention ("Virofree") can potentially reduce viral replication by inducing miR148b-5p, inhibiting $M^{pro}$, and suppressing cytokine storm; (A) miR-148b-5p expression levels were measured by qRT-PCR after 24 h treated with 33.3 μg/ml of Virofree (n=3). All data are presented as means±SD; (B) Virofree $IC_{50}$ of inhibiting recombinant SARS-CoV-2 $M^{pro}$ was determined and showed (μg/ml); (C) After treating PMA-differentiated THP-1 cells for 6 or 24 h, the cell medium was collected, and then ELISA was used to measure the amount of cytokine release. treatment of LPS 100 ng/ml alone in differentiated THP-1 cells was considered as the positive control (n=3). [All data are presented as means±SD. Statistical analysis was carried out with one-way ANOVA. * or **: significantly different from the corresponding control respectively with p<0.05 or 0.01].

In addition, as shown in FIG. 2, inhibition of viral replication and cytokine storm appear to be intracellular events. Moreover, the interruption of spike protein/ACE2 interaction (FIG. 3) and attenuation of viral infection (FIG. 4) are extracellular events. We speculate that this difference in targeting components might be explained by differences in required dosages for inhibiting viral replication, cytokine storm, and attenuation of viral infection.

Figure 5:
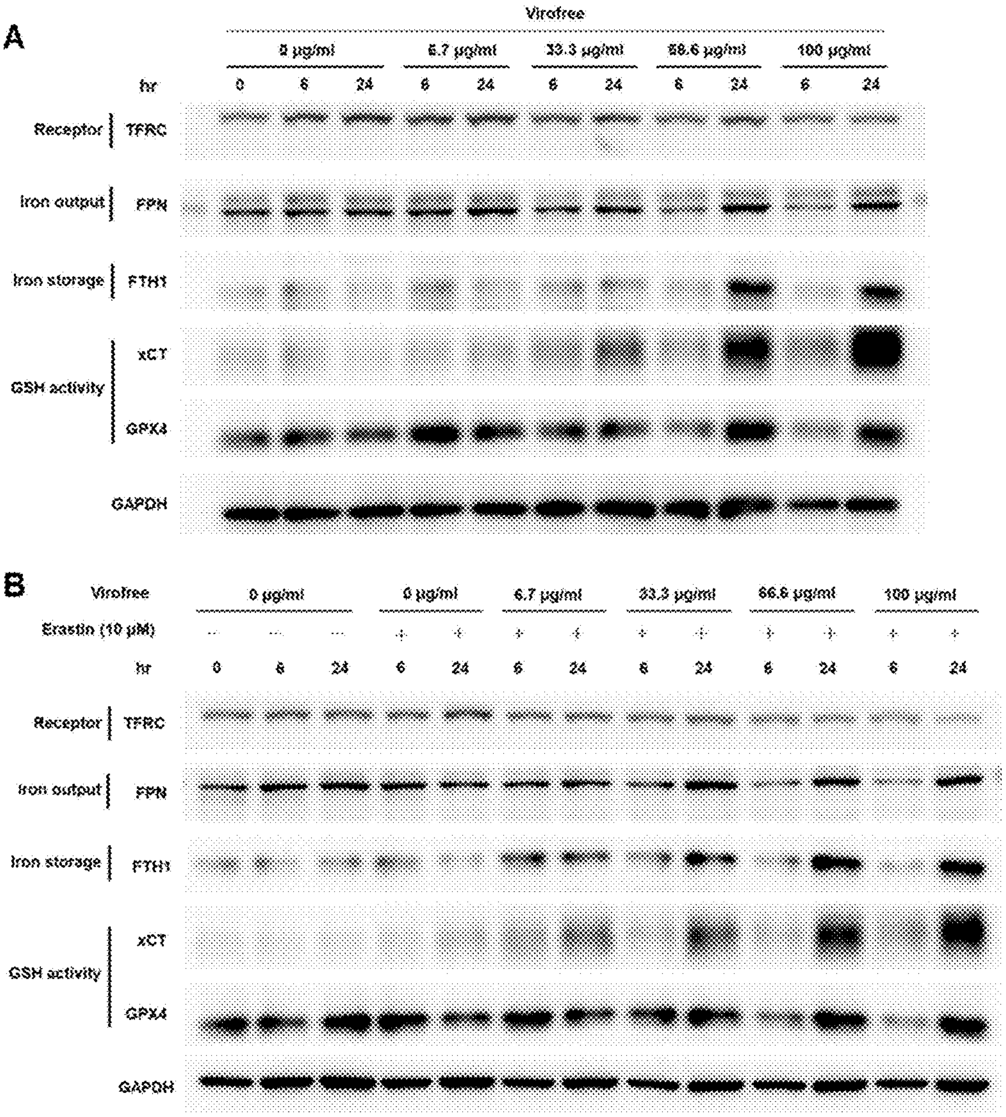
FIG. 5 shows the Virofree has the potential to reduce the labile iron pool and protect the cells from ferroptosis in THP-1-derived macrophages; (A) THP-1-derived macrophages received treatments of different concentrations of Virofree for 6, or 24 h, respectively. Whole-cell lysates were prepared and subjected to western blot analysis. GAPDH was used as an internal control (n=3); (B) THP-1-derived macrophages received treatments of different concentrations of Virofree in the presence of erastin (10 μM) for 6, or 24 h, respectively. Whole-cell lysates were prepared and subjected to western blot analysis. GAPDH was used as an internal control (n=3).

The inflammatory condition of COVID-19 patients is also associated with iron metabolism dysregulation [75]. However, excess intracellular iron can promote ROS production. System $xc^-$, the cystine/glutamate antiporter (a transmembrane protein complex containing SLC7A11 and SLC3A2 subunits) is increased for glutathione synthesis to inhibit cellular ROS production [76]. Intracellular iron, which is kept in relative balance by uptake and metabolism, can be exported out of the cell through FPN or be stored in Fe (III) via ferritin to prevent oxidative stress caused by excess free iron within cells. SARS-CoV-2 infection promotes iron accumulation in cells, which promotes ferroptosis and ultimately leads to organ failure. There is also evidence that SARS-CoV-2 can infect macrophages which involve in iron metabolism and inflammatory response [77] through certain mechanisms [78], indicating macrophages as an attractive therapeutic target. The experimental results showed that Virofree could enhance the expression levels of FTH1 and xCT (SLC7A11) in macrophages, and could reverse the downregulation of FPN and GPX4 expression levels caused by erastin (ferroptosis inducer) treatment [79], demonstrating the potential of Virofree to prevent macrophages from ferroptosis. Another finding is that Virofree downregulated TFRC expression levels in cells from bioinformatics analysis and experimental results (FIG. 5).

It was also reported in a study that TFRC directly interacts with the SARS-CoV-2 spike protein to mediate viral entry, also suggests that TFRC is an alternative receptor for SARS-CoV-2 cell entry [80]. Currently, no ACE2 inhibitors have been beneficial to COVID-19 patients and highlight TFRC as a promising anti-COVID-19 target.

Figure 16:
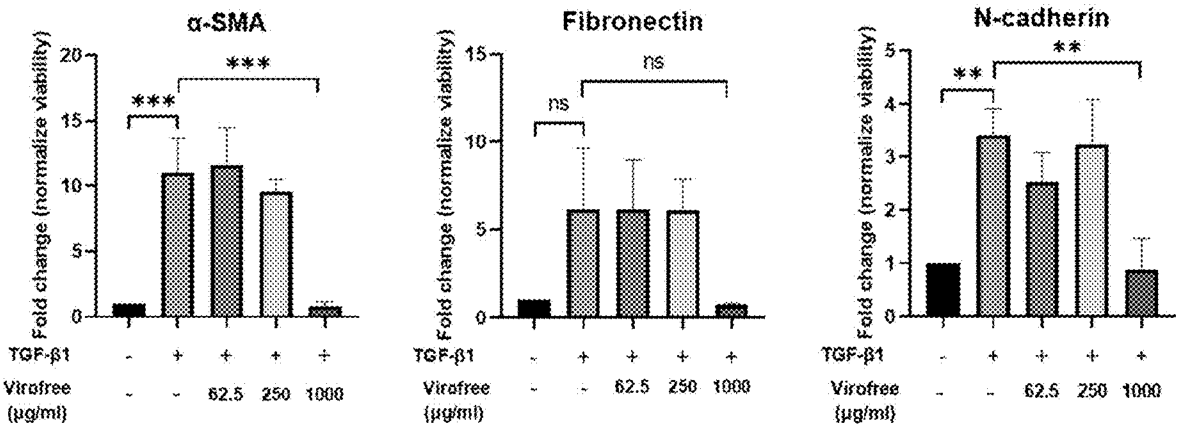
FIG. 16 shows the quantification and statistical analysis of Western blot shown in FIG. 6.

High serum levels of inflammatory cytokines and elevated ferritin in patients with severe COVID-19 correlate with disease severity and inflammation and iron-ion metabolic derangement [81, 82]. The main symptoms of severe SARS-CoV-2 infection include severe pneumonia and ARDS. Lung damages, including extensive interstitial and alveolar inflammatory infiltrates, alveolar septal thickening, vascular congestion, and pulmonary edema, were found after SARS-CoV-2 infection, which in some patients may be associated with the development of irreversible pulmonary fibrosis [83]. Previous cohort study also indicated that almost 87% of COVID-19 patients had pulmonary fibrosis after SARS-CoV-2 infection [84]. TGF-β1 plays an important role in the pathogenesis of fibrotic lung disease, by promoting fibroblast cells differentiation to myofibroblast cells [41], and stimulating the synthesis of ECM components, eventually leading to abnormal fibrosis [42]. Treatment of Virofree on TGF-β1-induced fibrosis LL29 cells for 48 h indicated that Virofree can significantly inhibit TGF-β1-induced α-SMA and N-cadherin protein expression, and notably reduce fibronectin (FIG. 6, FIG. 16).

Figure 17:
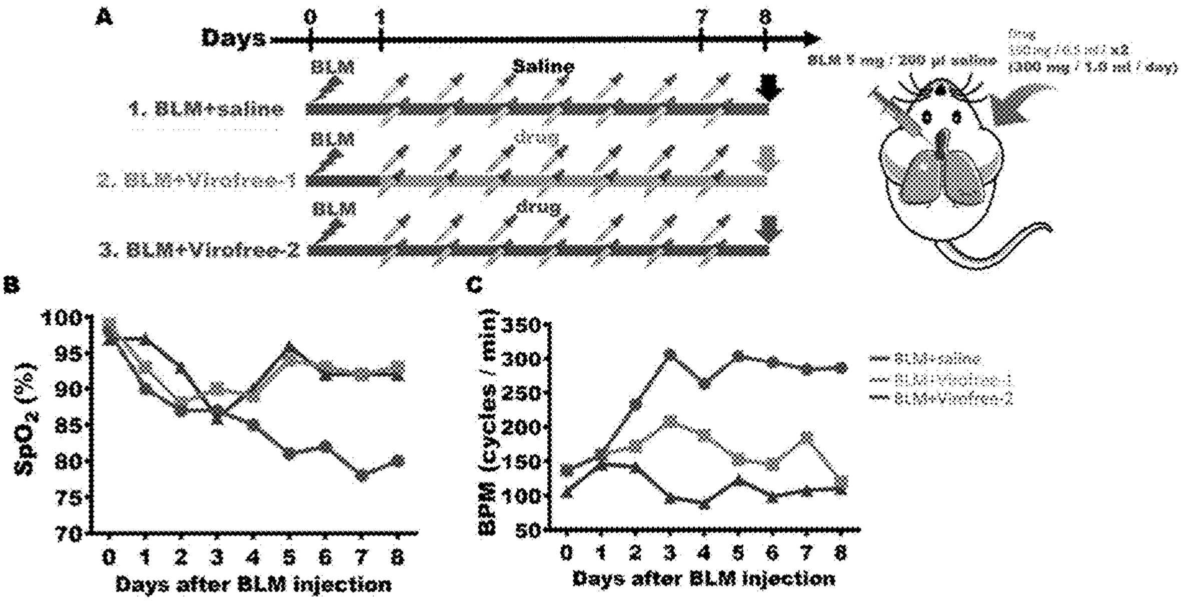
FIG. 17 shows the Virofree improved pulmonary function in BLM-induced ARDS rats; (A) experimental scheme of Virofree treatment; (B) Arterial blood oxygen saturation ($SpO_2$) and (C) Respiratory rate (BPM: Breath per min).
Figure 18:
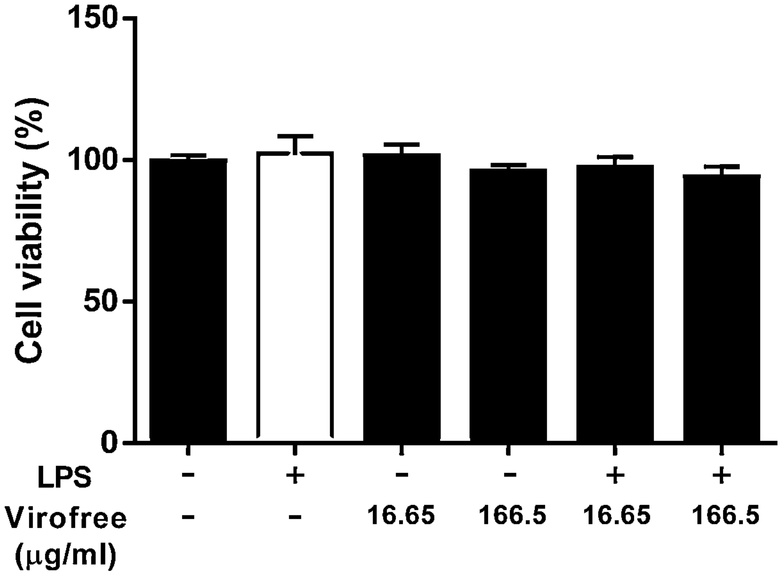
FIG. 18 shows the cytotoxicity of Virofree treatment on differentiated THP-1 cells; PMA-differentiated THP-1 cells were treated with Virofree, with or without LPS 100 ng/ml. After 24 h, an MTS assay was performed to measure cell viability; the group without any treatment was considered a control group (n=3).
Figure 19:
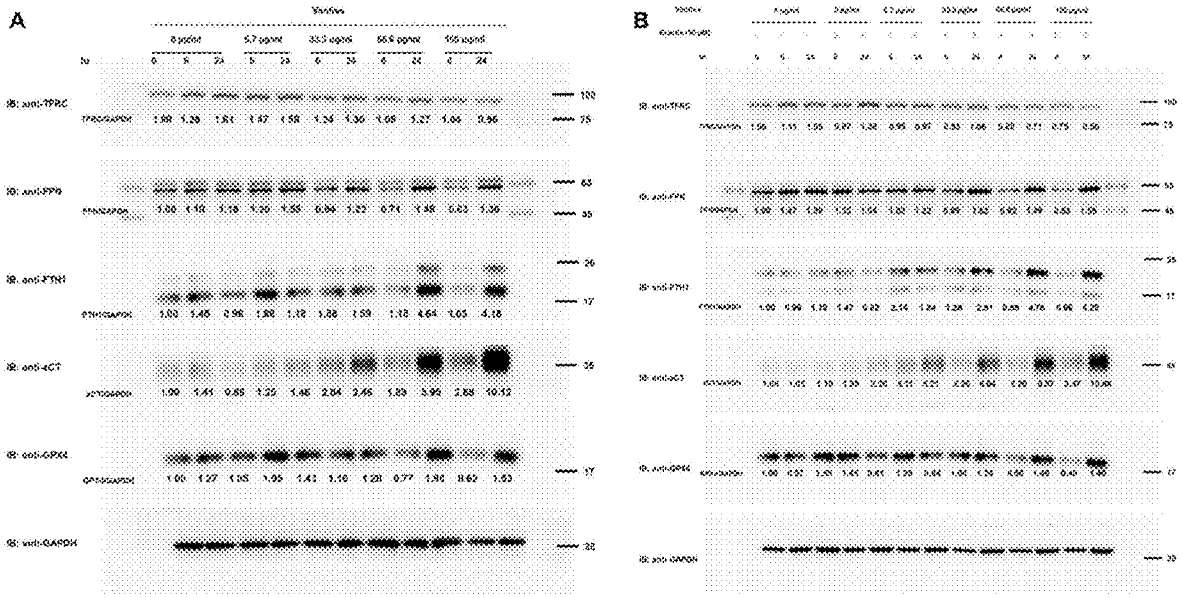
FIG. 19 shows the whole un-cropped images of the original Western blots shown in FIG. 5.
Figure 20:
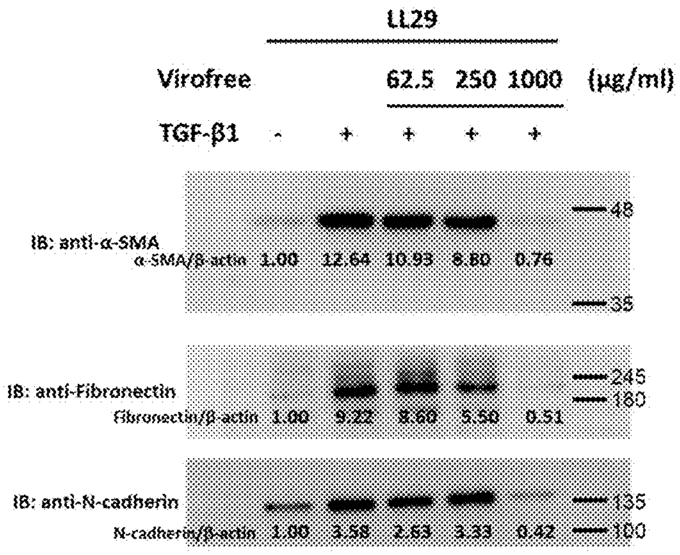
FIG. 20 shows the whole un-cropped images of the original Western blots shown in FIG. 6.

For a better simulation of the patients' condition, a BLM-induced ARDS rat model was used to investigate the effects of Virofree. Our preliminary observation showed that Virofree treatment improved the condition of ARDS rats by increasing arterial oxygen saturation and reducing breathing rate (FIG. 17). Since a high level of TNF-α is involved in the progression of ARDS, anti-TNF-α has been considered as one of the pivotal therapies for this disease [85]. That Virofree was able to decrease TNF-α secretion amount, fibrosis-related protein expression in vitro (FIG. 6, FIG. 16), and improve physiological indexes of ARDS rats in the preliminary in vivo results suggest that Virofree is a potential anti-COVID-19 and anti-fibrosis treatment. Further investigations with additional rats are needed to confirm its mechanisms in treating ARDS.

Recently, several therapeutic drugs for treating COVID-19 have been approved for Emergency Use Authorization, such as Nirmatrelvir/Ritonavir (Pfizer) or Molnupiravir (Merck). However, they can only target viral $M^{pro}$ or disrupt RNA replication, respectively. Due to the emergence of mutant strains which grow faster than the speed of drug development, it is necessary to discover and advance broad-spectrum drugs to target multiple risk factors caused by SARS-CoV-2.

Proinflammatory cytokines induce the formation of large amounts of nitric oxide (NO) by inducible nitric oxide synthase (iNOS), and compounds that inhibit NO production have anti-inflammatory effects. Some of the ingredients in Virofree include flavonoids, such as Quercetin, Hesperidin, Genistein, Daidzein, and Resveratrol, which elicit strong antioxidant and anti-inflammatory effects [13-15]. It has been reported that Quercetin, Genistein, and Daidzein can inhibit iNOS protein and NO production. These ingredients are also able to suppress the activation of NF-kB, which is activated by TNF-α [86] and triggers the activation of IL-6 [14]. In addition, Hesperidin has been proven to be beneficial against COVID-19 due to its immunomodulatory effects and antiviral activities, which result in inhibition of SARS-CoV-2 $M^{pro}$ [87]. Quercetin is another flavonoid with an antiviral effect against SARS-CoV-2 $M^{pro}$ [88]. Hence, Virofree, which consists of a combination of flavonoids with anti-inflammatory and antiviral properties, may have potential as a candidate herbal medicine against COVID-19.

In conclusion, the data suggest that Virofree can target various stages of viral entry and replication, especially against Delta and Omicron variants, as well as the following consequences including ferroptosis, cytokine storm, ARDS, and pulmonary fibrosis (FIG. 7). These findings emphasized the potential of Virofree as a multiple-function herbal medicine to reduce SARS-CoV-2 infection in the circumstance that there are no specific and effective drugs for new variants and to alleviate post-infection complications.

While this specification contains many specifics, these should not be construed as limitations on the scope of the invention or of what may be claimed, but rather as descriptions of features specific to particular embodiments or examples of the invention. Certain features that are described in this specification in the context of separate embodiments or examples can also be implemented in combination in a single embodiment.

REFERENCES

1. Holshue, M. L., et al., *First Case of* 2019 *Novel Coronavirus in the United States*. New England Journal of Medicine, 2020. 382(10): p. 929-936.
2. Mokhtari, T., et al., *COVID*-19 *and multiorgan failure: A narrative review on potential mechanisms*. Journal of Molecular Histology, 2020. 51(6): p. 613-628.
3. Lucas, C., et al., *Longitudinal analyses reveal immunological misfiring in severe COVID*-19. Nature, 2020. 584(7821): p. 463-469.
4. Wang, D., et al., *Clinical Characteristics of* 138 *Hospitalized Patients With* 2019 *Novel Coronavirus-Infected Pneumonia in Wuhan, China*. JAMA, 2020. 323(11): p. 1061-1069.
5. Wu, C., et al., *Risk Factors Associated With Acute Respiratory Distress Syndrome and Death in Patients With Coronavirus Disease* 2019 *Pneumonia in Wuhan, China*. JAMA internal medicine, 2020. 180(7): p. 934-943.
6. Cheng, L., et al., *Ferritin in the coronavirus disease* 2019 (*COVID*-19): *A systematic review and meta-analysis*. J Clin Lab Anal, 2020. 34(10): p. e23618.
7 Gasparello, J., A. Finotti, and R. Gambari, *Tackling the COVID*-19 *"cytokine storm" with microRNA mimics directly targeting the* 3*'UTR of pro-inflammatory mRNAs*. Medical Hypotheses, 2021. 146: p. 110415.
8. Palanisamy, V., et al., *Control of Cytokine mRNA Expression by RNA-binding Proteins and microRNAs*. Journal of Dental Research, 2012. 91(7): p. 651-658.
9. *Center for Drug Evaluation and Research Response to Coronavirus* (*COVID*-19), *in U.S. Food and Drug Administration*. Jan. 1, 2020-Sep. 30, 2021: https://www.fda.gov/drugs/coronavirus-covid-19-drugs/center-drug-evaluation-and-research-response-coronavirus-covid-19-infographic.
10. Hossain, M. K., M. Hassanzadeganroudsari, and V. Apostolopoulos, *The emergence of new* strains *of SARS-CoV*-2. *What does it mean for COVID*-19 *vaccines*? Expert review of vaccines, 2021. 20(6): p. 635-638.

11. Huang, T. H., et al., *In silico identification of thiostrepton as an inhibitor of cancer stem cell growth and an enhancer for chemotherapy in non-small-cell lung cancer*. J Cell Mol Med, 2019. 23(12): p. 8184-8195.
12. Subramanian, A., et al., *Gene set enrichment analysis: A knowledge-based approach for interpreting genome-wide expression profiles*. Proceedings of the National Academy of Sciences, 2005. 102(43): p. 15545.
13. Parhiz, H., et al., *Antioxidant and Anti-Inflammatory Properties of the Citrus Flavonoids Hesperidin and Hesperetin: An Updated Review of their Molecular Mechanisms and Experimental Models*. Phytotherapy Research, 2015. 29(3): p. 323-331.
14. Hämäläinen, M., et al., *Anti-inflammatory effects of flavonoids: genistein, kaempferol, quercetin, and daidzein inhibit STAT-*1 *and NF-kappaB activations, whereas flavone, isorhamnetin, naringenin, and pelargonidin inhibit only NF-kappaB activation along with their inhibitory effect on iNOS expression and NO production in activated macrophages*. Mediators of inflammation, 2007. 2007: p. 45673-45673.
15. de Sá. Coutinho, D., et al., *Anti-Inflammatory Effects of Resveratrol: Mechanistic Insights*. International journal of molecular sciences, 2018. 19(6): p. 1812.
16. Kanehisa, M., et al., *KEGG: integrating viruses and cellular organisms*. Nucleic Acids Research, 2020. 49(D1): p. D545-D551.
17. Ashburner, M., et al., *Gene ontology: tool for the unification of biology. The Gene Ontology Consortium*. Nature genetics, 2000. 25(1): p. 25-29.
18. Du, P., et al., *From disease ontology to disease-ontology lite: statistical methods to adapt a general-purpose ontology for the test of gene-ontology associations*. Bioinformatics, 2009. 25(12): p. i63-8.
19. Schriml, L. M., et al., *Human Disease Ontology* 2018 *update: classification, content and workflow expansion*. Nucleic Acids Res, 2019. 47(D1): p. D955-d962.
20. de Gonzalo-Calvo, D., et al., *Circulating microRNA profiles predict the severity of COVID-*19 *in hospitalized patients*. Transl Res, 2021. 236: p. 147-159.
21. Farr, R. J., et al., *Altered microRNA expression in COVID-*19 *patients enables identification of SARS-CoV-*2 *infection*. PLoS Pathog, 2021. 17(7): p. e1009759.
22. Lee, Y.-R., et al., *Honeysuckle Aqueous Extracts Induced let-*7*a Suppress EV*71 *Replication and Pathogenesis In Vitro and In Vivo and Is Predicted to Inhibit SARS-CoV-*2. Viruses, 2021. 13(2).
23. Dai, W., et al., *Structure-based design of antiviral drug candidates targeting the SARS-CoV-*2 *main protease*. Science, 2020. 368(6497): p. 1331.
24. Shi, T. H., et al., *Andrographolide and its fluorescent derivative inhibit the main proteases of* 2019*-nCoV and SARS-CoV through covalent linkage*. Biochem Biophys Res Commun, 2020. 533(3): p. 467-473.
25. Muruato, A. E., et al., *A high-throughput neutralizing antibody assay for COVID-*19 *diagnosis and vaccine evaluation*. Nature Communications, 2020. 11(1): p. 4059.
26. Maza, E., *In Papyro Comparison of TMM* (*edgeR*), *RLE* (*DESeq*2), *and MRN Normalization Methods for a Simple Two-Conditions-Without-Replicates RNA-Seq Experimental Design*. 2016. 7.
27. Robinson, M. D., D. J. McCarthy, and G. K. Smyth, *edgeR: a Bioconductor package for differential expression analysis of digital gene expression data*. Bioinformatics, 2010. 26(1): p. 139-40.
28. Wang, L., et al., *DEGseq: an R package for identifying differentially expressed genes from RNA-seq data*. Bioinformatics, 2010. 26(1): p. 136-8.
29. Subramanian, A., et al., *Gene set enrichment analysis: A knowledge*-based approach for interpreting genome-wide expression profiles. 2005. 102(43): p. 15545-15550.
30. Leek, J. T., et al., *The sva package for removing batch effects and other unwanted variation in high-throughput experiments*. Bioinformatics, 2012. 28(6): p. 882-3.
31. Nair, A. B. and S. Jacob, *A simple practice guide for dose conversion between animals and human*. Journal of basic and clinical pharmacy, 2016. 7(2): p. 27-31.
32. Blanco-Melo, D., et al., *Imbalanced Host Response to SARS-CoV-*2 *Drives Development of COVID-*19. Cell, 2020. 181(5): p. 1036-1045.e9.
33. Xie, C., et al., *Therapeutic potential of C*1632 *by inhibition of SARS-CoV-*2 *replication and viral-induced inflammation through upregulating let-*7. Signal Transduction and Targeted Therapy, 2021. 6(1): p. 84.
34. V'Kovski, P., et al., *Coronavirus biology and replication: implications for SARS-CoV-*2. Nat Rev Microbiol, 2021. 19(3): p. 155-170.
35. Choudhary, S., K. Sharma, and O. Silakari, *The interplay between inflammatory pathways and COVID-*19*: A critical review on pathogenesis and therapeutic options*. Microb Pathog, 2021. 150: p. 104673.
36. Ortega, V., et al., *Addicted to sugar: roles of glycans in the order Mononegavirales*. Glycobiology, 2018. 29.
37. Buchrieser, J., et al., *Syncytia formation by SARS-CoV-*2*-infected cells*. EMBO J, 2020. 39(23): p. e106267.
38. Cheng, Y. W., et al., *Furin Inhibitors Block SARS-CoV-*2 *Spike Protein Cleavage to Suppress Virus Production and Cytopathic Effects*. Cell Rep, 2020. 33(2): p. 108254.
39. Li, X., et al., *Molecular immune pathogenesis and diagnosis of COVID-*19. Journal of Pharmaceutical Analysis, 2020. 10(2): p. 102-108.
40. Michalski, J. E., J. S. Kurche, and D. A. Schwartz, *From ARDS to pulmonary fibrosis: the next phase of the COVID-*19 *pandemic*? Translational Research, 2022. 241: p. 13-24.
41. Yue, X., B. Shan, and J. A. Lasky, *TGF-*β*: Titan of Lung Fibrogenesis*. Current enzyme inhibition, 2010. 6(2): p. 10.2174/10067.
42. Hinz, B., et al., *The myofibroblast—One function, multiple origins*. American Journal of Pathology, 2007. 170 (6): p. 1807-1816.
43. Ader, F., et al., *Remdesivir plus standard of care versus standard of care alone for the treatment of patients admitted to hospital with COVID-*19 (*DisCoVeRy*)*: a phase* 3*, randomised, controlled, open-label trial*. Lancet Infect Dis, 2021.
44. Mozaffari, E., et al., *Remdesivir treatment in hospitalized patients with COVID-*19*: a comparative analysis of in-hospital all-cause mortality in a large multi-center observational cohort*. Clinical Infectious Diseases, 2021.
45. Goldman, J. D., et al., *Remdesivir for* 5 *or* 10 *Days in Patients with Severe Covid-*19. 2020. 383(19): p. 1827-1837.
46. Cao, B., et al., *A Trial of Lopinavir-Ritonavir in Adults Hospitalized with Severe Covid-*19. 2020. 382(19): p. 1787-1799.
47. Wong, C. K. H., et al., *Clinical outcomes of different therapeutic options for COVID-*19 *in two Chinese case cohorts: A propensity-score analysis*. EClinicalMedicine, 2021. 32.

48. Karim, S. S. A. and Q. A. Karim, *Omicron SARS-CoV-2 variant: a new chapter in the COVID-19 pandemic*. The Lancet, 2021. 398(10317): p. 2126-2128.
49. Greasley, S. E., et al., *Structural basis for Nirmatrelvir in vitro efficacy against the Omicron variant of SARS-CoV-2*. bioRxiv, 2022: p. 2022.01.17.476556.
50. Ratre, Y. K., et al., *Molecular mechanism, diagnosis, and potential treatment for novel coronavirus (COVID-19): a current literature review and perspective*. 3 Biotech, 2021. 11(2): p. 94.
51. Huff, S., et al., *Discovery and Mechanism of SARS-CoV-2 Main Protease Inhibitors*. Journal of Medicinal Chemistry, 2021.
52. Jin, Z., et al., *Structure of Mpro from SARS-CoV-2 and discovery of its inhibitors*. Nature, 2020. 582(7811): p. 289-293.
53. Zhao, K., et al., *Serum Iron Level as a Potential Predictor of Coronavirus Disease 2019 Severity and Mortality: A Retrospective Study*. Open Forum Infect Dis, 2020. 7(7): p. ofaa250.
54. Hippchen, T., et al., *Hypoferremia is Associated With Increased Hospitalization and Oxygen Demand in COVID-19 Patients*. Hemasphere, 2020. 4(6): p. e492.
55. Tian, M., et al., *HIF-1α promotes SARS-CoV-2 infection and aggravates inflammatory responses to COVID-19*. Signal Transduction and Targeted Therapy, 2021. 6(1): p. 308.
56. Serebrovska, Z. O., et al., *Hypoxia, HIF-1α, and COVID-19: from pathogenic factors to potential therapeutic targets*. Acta Pharmacologica Sinica, 2020. 41(12): p. 1539-1546.
57. Alfarouk, K. O., et al., *Pathogenesis and Management of COVID-19*. 2021. 11(2): p. 77-93.
58. Pandey, V., et al., *COVID-19: An update of current knowledge (Review)*. World Acad Sci J, 2021. 3(2): p. 15.
59. Sardar, R., et al., *Comparative analyses of SAR-CoV2 genomes from different geographical locations and other coronavirus family genomes reveals unique features potentially consequential to host-virus interaction and pathogenesis*. 2020: p. 2020.03.21.001586.
60. Chauhan, N., et al., *COVID-19: fighting the invisible enemy with microRNAs*. Expert Rev Anti Infect Ther, 2021. 19(2): p. 137-145.
61. Chen, X. M., et al., *A cellular micro-RNA, let-7i, regulates Toll-like receptor 4 expression and contributes to cholangiocyte immune responses against Cryptosporidium parvum infection*. J Biol Chem, 2007. 282(39): p. 28929-28938.
62. Guo, H., et al., *DEF Cell-Derived Exosomal miR-148a-5p Promotes DTMUV Replication by Negative Regulating TLR3 Expression*. 2020. 12(1): p. 94.
63. Milenkovic, D., et al., *Polyphenols Could Prevent SARS-CoV-2 Infection by Modulating the Expression of miRNAs in the Host Cells*. Aging Dis, 2021. 12(5): p. 1169-1182.
64. Sacar Demirci, M. D. and A. Adan, *Computational analysis of microRNA-mediated interactions in SARS-CoV-2 infection*. PeerJ, 2020. 8: p. e9369.
65. Wang, Y., et al., *Remdesivir in adults with severe COVID-19: a randomised, double-blind, placebo-controlled, multicentre trial*. The Lancet, 2020. 395(10236): p. 1569-1578.
66. Hegyi, A. and J.J.J.o.g.v. Ziebuhr, *Conservation of substrate specificities among coronavirus main proteases*. 2002. 83(3): p. 595-599.
67. Pillaiyar, T., et al., *An overview of severe acute respiratory syndrome-coronavirus (SARS-CoV) 3CL protease inhibitors: peptidomimetics and small molecule chemotherapy*. 2016. 59(14): p. 6595-6628.
68. Callaway, E., *Omicron likely to weaken COVID vaccine protection*. Nature, 2021. 600(7889): p. 367-368.
69. Lin, L., et al., *Syncytia formation during SARS-CoV-2 lung infection: a disastrous unity to eliminate lymphocytes*. Cell Death & Differentiation, 2021. 28(6): p. 2019-2021.
70. Braga, L., et al., *Drugs that inhibit TME16 proteins block SARS-CoV-2 spike-induced syncytia*. Nature, 2021. 594(7861): p. 88-93.
71. Rajah, M. M., et al., *SARS-CoV-2 Alpha, Beta, and Delta variants display enhanced Spike-mediated syncytia formation*. The EMBO journal, 2021. 40(24): p. e108944-e108944.
72. Hoffmann, M., et al., *SARS-CoV-2 Cell Entry Depends on ACE2 and TMPRSS2 and Is Blocked by a Clinically Proven Protease Inhibitor*. Cell, 2020. 181(2): p. 271-280.e8.
73. Suzuki, Y. J. and S. G. Gychka, *SARS-CoV-2 Spike Protein Elicits Cell Signaling in Human Host Cells: Implications for Possible Consequences of COVID-19 Vaccines*. Vaccines, 2021. 9(1): p. 36.
74. Suresh, S. J. and Y. J. Suzuki, *SARS-CoV-2 Spike Protein and Lung Vascular Cells*. Journal of Respiration, 2021. 1(1).
75. Chifman, J., R. Laubenbacher, and S. V. Torti, *A systems biology approach to iron metabolism*. Advances in experimental medicine and biology, 2014. 844: p. 201-225.
76. Sato, M., et al., *The ferroptosis inducer erastin irreversibly inhibits system xc- and synergizes with cisplatin to increase cisplatin's cytotoxicity in cancer cells*. Scientific Reports, 2018. 8(1): p. 968.
77. Soares, M. P. and I. Hamza, *Macrophages and Iron Metabolism*. Immunity, 2016. 44(3): p. 492-504.
78. Abassi, Z., et al., *The Lung Macrophage in SARS-CoV-2 Infection: A Friend or a Foe?* 2020. 11(1312).
79. Shibata, Y., et al., *Erastin, a ferroptosis-inducing agent, sensitized cancer cells to X-ray irradiation via glutathione starvation in vitro and in vivo*. PLoS One, 2019. 14(12): p. e0225931.
80. Tang, X., et al., *Transferrin receptor is another receptor for SARS-CoV-2 entry*. 2020: p. 2020.10.23.350348.
81. Del Valle, D. M., et al., *An inflammatory cytokine signature predicts COVID-19 severity and survival*. Nature Medicine, 2020. 26(10): p. 1636-1643.
82. Yang, M. and C. L. Lai, *SARS-CoV-2 infection: can ferroptosis be a potential treatment target for multiple organ involvement?* Cell Death Discovery, 2020. 6(1): p. 130.
83. Yang, Q., et al., *Inhibition of SARS-CoV-2 viral entry upon blocking N- and O-glycan elaboration*. eLife, 2020. 9: p. e61552.
84. Suzuki, Y. J., et al., *SARS-CoV-2 spike protein-mediated cell signaling in lung vascular cells*. Vascular pharmacology, 2021. 137: p. 106823-106823.
85. Malaviya, R., J. D. Laskin, and D. L. Laskin, *Anti-TNFα therapy in inflammatory lung diseases*. Pharmacology & therapeutics, 2017. 180: p. 90-98.
86. Pozniak, P. D., M. K. White, and K. Khalili, *TNF-α/NF-κB signaling in the CNS: possible connection to EPHB2*. Journal of neuroimmune pharmacology: the official journal of the Society on NeuroImmune Pharmacology, 2014. 9(2): p. 133-141.
87. Ngwa, W., et al., *Potential of Flavonoid-Inspired Phytomedicines against COVID-19*. Molecules (Basel, Switzerland), 2020. 25(11): p. 2707.

88. Sharma, A., et al., *In-silico screening of plant-derived antivirals against main protease, 3CL(pro) and endoribonuclease, NSP15 proteins of SARS-CoV-2*. Journal of biomolecular structure & dynamics, 2022. 40(1): p. 86-100.

What is claimed is:

1. A capsule consisting essentially of a grape seed extract, an acerola cherry extract, an olive leaf extract, a marigold extract, a green tea extract, a pomegranate extract, a yeast beta-glucan and a soybean extract.

2. The capsule of claim 1, consisting essentially of 10 wt %-50 wt % of the grape seed extract, 5 wt %-30 wt % of the acerola cherry extract, 5 wt %-30 wt % of the olive leaf extract, 1 wt %-20 wt % of the marigold extract, 1 wt %-20 wt % of the green tea extract, 1 wt %-20 wt % of the pomegranate extract, 1 wt %-20 wt % of the yeast beta-glycan, and 1 wt %-20 wt % of the soybean extract, based on the total weight of the capsule.

3. The capsule of claim 1, wherein the capsule consists essentially of about 250 mg grape seed extract, about 180 mg acerola cherry extract, about 160 mg olive leaf extract, about 90 mg marigold extract, about 80 mg green tea extract, about 80 mg pomegranate extract, about 80 mg yeast beta-glycan and about 80 mg soybean extract.

4. The capsule of claim 1, wherein the capsule consists essentially of about 25% grape seed extract, about 18% acerola cherry extract, about 16% olive leaf extract, about 9% marigold extract, about 8% green tea extract, about 8% pomegranate extract, about 8% yeast beta-glycan, and about 8% soybean extract, based on the total weight of the capsule.

* * * * *